(12) United States Patent
Han et al.

(10) Patent No.: US 11,794,143 B2
(45) Date of Patent: Oct. 24, 2023

(54) AIR PURIFIER

(71) Applicants: Guangdong Midea White Home Appliance Technology Innovation Center Co., Ltd., Foshan (CN); Midea Group Co., Ltd., Foshan (CN)

(72) Inventors: Yunqing Han, Foshan (CN); Zulin Pu, Foshan (CN); Hui Zhang, Foshan (CN)

(73) Assignees: GUANGDONG MIDEA WHITE HOME APPLIANCE TECHNOLOGY INNOVATION CENTER CO., LTD., Foshan (CN); MIDEA GROUP CO., LTD., Foshan (CN)

( * ) Notice: Subject to any disclaimer, the term of this patent is extended or adjusted under 35 U.S.C. 154(b) by 412 days.

(21) Appl. No.: 17/145,140

(22) Filed: Jan. 8, 2021

(65) Prior Publication Data

US 2021/0129070 A1 May 6, 2021

Related U.S. Application Data

(63) Continuation of application No. PCT/CN2019/122739, filed on Dec. 3, 2019.

(30) Foreign Application Priority Data

Dec. 14, 2018 (CN) .......................... 201811536593.8

(51) Int. Cl.
*B01D 47/16* (2006.01)
*A61L 9/14* (2006.01)
(Continued)

(52) U.S. Cl.
CPC .............. *B01D 47/16* (2013.01); *A61L 9/145* (2013.01); *A61L 9/205* (2013.01); *B01D 46/26* (2013.01);
(Continued)

(58) Field of Classification Search
CPC ........ B01D 47/16; B01D 47/06; B01D 53/74; A61L 9/145; A61L 9/205
See application file for complete search history.

(56) References Cited

U.S. PATENT DOCUMENTS 6,217,637 B1 * 4/2001 Toney .................. B01D 33/073
55/284
7,833,305 B1 * 11/2010 Studer ................ B01D 46/2411
55/467

(Continued)

FOREIGN PATENT DOCUMENTS

| CN | 101039732 A | 9/2007 |
|----|-------------|--------|
| CN | 201140135 Y | 10/2008 |

(Continued)

OTHER PUBLICATIONS

Midea Group Co., Ltd., First JP Office Action, JP Patent Application No. 2021-521876, dated Feb. 22, 2022, 6 pgs.

(Continued)

*Primary Examiner* — Kevin Joyner
*Assistant Examiner* — Priscilla Browning
(74) *Attorney, Agent, or Firm* — Morgan, Lewis & Bockius LLP

(57) ABSTRACT

An air purifier comprising: a housing provided with air inlets and air outlets and defining an accommodating cavity, wherein the air inlets are located on the side walls of the housing; a water supply module arranged within the accommodating cavity and defining a water storage cavity; a purifying module arranged within the accommodating cavity and located on the water supply module, the purifying module comprising: a purifying assembly rotatably disposed within the accommodating cavity, a water distribution assembly for guiding water in the water supply module to flow upwards and distributing water to the purifying assembly, and a driving device located on the purifying assembly (Continued)

and connected with the purifying assembly; and an air discharge module disposed within the accommodating cavity and located on the purifying module.

41 Claims, 24 Drawing Sheets

(51) Int. Cl.
    *A61L 9/20*         (2006.01)
    *B01D 46/26*     (2006.01)
    *B01D 47/06*     (2006.01)
    *B01D 53/00*     (2006.01)
    *B01D 53/86*     (2006.01)
    *C02F 1/461*     (2023.01)
    *B01D 50/60*     (2022.01)

(52) U.S. Cl.
    CPC ............. *B01D 47/06* (2013.01); *B01D 50/60* (2022.01); *B01D 53/007* (2013.01); *B01D 53/8668* (2013.01); *C02F 1/46109* (2013.01); *A61L 2209/12* (2013.01); *B01D 2255/802* (2013.01); *B01D 2257/708* (2013.01); *B01D 2259/804* (2013.01)

(56) References Cited

U.S. PATENT DOCUMENTS

| | | | |
|---|---|---|---|
| 9,080,780 B2 * | 7/2015 | Lee | A61L 9/205 |
| 2006/0230713 A1 | 10/2006 | Kim | |
| 2008/0028936 A1 * | 2/2008 | Takahashi | F24F 8/10 |
| | | | 96/25 |
| 2008/0044892 A1 * | 2/2008 | Wu | B01D 53/84 |
| | | | 435/292.1 |
| 2010/0201007 A1 * | 8/2010 | Tsuda | F24F 6/06 |
| | | | 74/63 |
| 2017/0261216 A1 | 9/2017 | Moroga et al. | |
| 2018/0221805 A1 * | 8/2018 | Bae | B01D 46/58 |
| 2018/0339258 A1 | 11/2018 | Jeon | |

FOREIGN PATENT DOCUMENTS

| | | |
|---|---|---|
| CN | 203564935 U | 4/2014 |
| CN | 204447631 U | 7/2015 |
| CN | 106247445 A | 12/2016 |
| CN | 106556072 A | 4/2017 |
| CN | 107726478 A | 2/2018 |
| CN | 207262576 U | 4/2018 |
| CN | 207493403 U | 6/2018 |
| CN | 108371863 A | 8/2018 |
| CN | 108744814 A | 11/2018 |
| CN | 208804811 U | 4/2019 |
| CN | 209451555 U | 10/2019 |
| EP | 0096451 A1 | 12/1983 |
| EP | 3412980 A1 | 12/2018 |
| JP | S 5973027 A | 4/1984 |
| JP | H 10127742 A | 5/1998 |
| JP | 2002119844 A | 4/2002 |
| JP | 2010046358 A | 3/2010 |
| JP | 2018200164 A | 12/2018 |
| JP | 2021529931 A | 11/2021 |
| JP | 2021530353 A | 11/2021 |
| KR | 20180130431 A | 12/2018 |
| WO | WO 2006049470 A2 | 5/2006 |

OTHER PUBLICATIONS

Guangdong Midea White Home Appliance Technology Innovation Center Co., Ltd., et al., Extended European Search Report, EP Application No. 19895480.2, Jun. 22, 2021, 7 pgs.
Guangdong Meidi White Household Appliances Technology Innovation Center Co., Ltd., The Second Office Action, CN Application No. 201811536593.8, dated Apr. 30, 2021, 10 pgs.
International Search Report and Written Opinion, PCT/CN2019/122739, dated Mar. 4, 2020, 10 pgs.
Guangdong Midea White Goods Technology Innovation Center Co. Ltd., First Office Action, CN201811536593.8, dated Nov. 30, 2020, 19 pgs.
Unknown, cited as evidence for common knowledge, "Fluid conveying Machinery," publication date Mar. 31, 2016, 17 pgs.
Unknown, cited as evidence for common knowledge, "Return Air Grille and Air Supply Shutters," publication date May 31, 1995, 2 pgs.
Unknown, cited as evidence for common knowledge, "Screw Pump," publication date Mar. 1, 2014, 18 pgs.
Midea Group Co., Ltd., Written Opinion, PCT/CN2019/122739, dated Mar. 4, 2020, 9 pgs.

* cited by examiner

AIR PURIFIER

CROSS-REFERENCE TO RELATED APPLICATION

This application is a continuation of PCT International Application Serial No. PCT/CN2019/122739, filed Dec. 3, 2019, which claims priority to Chinese Patent Application No. 201811536593.8, filed on Dec. 14, 2018, each of which is hereby incorporated by reference in its entirety.

TECHNICAL FIELD

The disclosure relates to the technical field of purifying equipment, and in particular to an air purifier.

BACKGROUND

Purification equipment in the related technology purifies the air only by a filter sieve, the purification efficiency will be reduced after being used for a period of time. The filter sieve needs to be replaced regularly, which is not only inconvenient to use, but also has high maintenance cost.

SUMMARY

The disclosure aims to solve at least one of the technical problems existing in the related technology.

For this purpose, the disclosure provides an air purifier, which is convenient to use and low in cost.

The air purifier according to embodiments of the disclosure includes: a housing, a water supply member, a purifying member and an air moving member. The housing is provided with an air inlet and an air outlet, and the air inlet is located on the side wall of the housing. The housing defines an accommodating cavity communicating the air inlet with the air outlet. The water supply member is arranged in the accommodating cavity, and a water storage cavity is defined in the water supply member. The purifying member is arranged in the accommodating cavity and is located above the water supply member to purify the air. The purifying member includes a purifying assembly rotatably arranged in the accommodating cavity, a water distribution assembly for guiding water in the water supply member to flow upwards and distributing water towards the purifying assembly, and a driving device located above the purifying assembly and connected with the purifying assembly to drive the purifying assembly to rotate. The air moving member is arranged in the accommodating cavity and is located above the purifying member.

The air purifier according to embodiments of the disclosure may continuously and efficiently purify the solid, liquid and gaseous pollutants in the air without attenuation. The number of times of replacing a filter sieve in the air moving member is fewer, even it is not necessary to replace the filter sieve regularly, but only need to replace the water in the water storage cavity regularly, so it is easy to use and the cost is reduced. Moreover, the air purifier has the advantages of small volume, low pressure loss, low energy consumption and high efficiency.

According to an embodiment of the disclosure, the purifying assembly includes: a rotary capturing member and a rotary purifying member. The rotary capturing member and the rotary purifying member rotate in the accommodating cavity. The rotary purifying member is spaced apart from the side wall of the housing. The rotary capturing member is located above the rotary purifying member.

According to an example of the disclosure, the purifying assembly includes multiple stages. Each stage of the purifying assembly includes the rotary capturing member and the rotary purifying member. The multiple stages of the purifying assembly are successively connected to one another in an airflow direction.

According to examples of the disclosure, the rotary capturing member is in the form of a rotary disk, and the rotary purifying member is in the form of a rotary drum. A side wall of the rotary cylinder is provided with a first mesh, At least a portion of the rotary disk, located between the rotary cylinder and the housing in a radial direction, is provided with a second mesh.

In some examples, the purifying assembly includes: a rotary disk and a cylinder. The rotary disk includes a first rotary disk and a second rotary disk. The first rotary disk and the second rotary disk are rotatable in opposite directions with respect to one another. The first rotary disk is provided with a third mesh. The second rotary disk is provided with a fourth mesh. The second rotary disk is arranged above the first rotary disk and is spaced apart from the first rotary disk in an axial direction. The cylinder is arranged between the first rotary disk and the second rotary disk, and the outer circumferential wall of the cylinder is a cylindrical surface and is spaced apart from the side wall of the housing.

According to another embodiment of the disclosure, the water distribution assembly is arranged below the purifying assembly. The water distribution assembly includes: a water inlet pipe and a water driving member. A water discharge end of the water inlet pipe is provided with a plurality of water injection nozzles, or the water discharge end of the water inlet pipe is in the form of an atomizing nozzle. The water driving member is connected with the water inlet pipe to drive water in the water storage cavity to flow upwards.

In some examples, the water discharge end of the water inlet pipe extends into the purifying assembly.

In some examples, the water discharge end of the water inlet pipe is located below the purifying assembly and is spaced apart from the purifying assembly in a vertical direction.

In some examples, the water driving member includes: a water conveying member and a connector. The water conveying member is movably arranged in the water inlet pipe to convey liquid upwards. The water conveying member is connected with the purifying assembly through the connector.

In an example, the water conveying member is a screw. The screw is configured to rotate synchronously with the purifying assembly in the water inlet pipe. A conveying space is defined between the screw and the inner wall of the water inlet pipe. The screw presses the water in the water storage cavity into the conveying space to convey the water upwards.

In an example, the water driving member is a water pump, and the water pump is connected with a water inflow end of the water inlet pipe.

According to another example of the disclosure, the water distribution assembly includes a partition tube. The partition tube is located below the purifying assembly. The partition tube is arranged around the water inlet pipe, and is coaxial with the water inlet pipe and spaced apart from the water inlet pipe. A lee area is defined between the water inlet pipe and the partition tube.

According to yet another embodiment of the disclosure, the purifying member includes: a guide member. The guide member is arranged below the purifying assembly along the circumferential direction of the housing. The guide member collects liquid splashed on an inner wall of the accommodating cavity by the purifying assembly and guides the liquid towards the water supply member.

Further, the guide member includes: an annular water guide part and a flow guider. The air inlet is located below the purifying assembly. The annular water guide part is arranged between the purifying assembly and the air inlet. The annular water guide part and the inner wall of the accommodating cavity define a water guide groove. The water guide groove is provided with a water guide mouth. The flow guider axially extends along the inner wall of the accommodating cavity. The flow guider is arranged on the inner wall of the accommodating cavity and defines a flow guide channel together with the inner wall of the accommodating cavity. The flow guide channel is in communication with the water guide mouth.

Further, the annular water guide part includes: an annular base plate which forms the bottom wall of the water guide groove, and an annular baffle, which is connected with the annular base plate in the circumferential direction and is spaced apart from the inner wall of the accommodating cavity in the radial direction. The inner wall of the accommodating cavity, the annular base plate and the annular baffle jointly define the water guide groove.

According to yet another embodiment of the disclosure, the purifying member includes: a photocatalyst layer. The photocatalyst layer is arranged on at least one of the surface of the purifying member and the inner wall surface of the accommodating cavity, and configured to be exposed to light.

In some examples, the purifying member includes: a sterilization lamp, which is arranged in the accommodating cavity to illuminate the photocatalyst layer.

According to yet another embodiment of the disclosure, a portion of the side wall of the housing radially facing the purifying member forms a transparent part.

Further, the purifying member includes a first grille, an outer circumference of the first grille is connected with the lower edge of the transparent part, and an inner circumference of the first grille extends radially towards the water inlet pipe.

According to yet another embodiment of the disclosure, the driving device includes: a motor which has a motor shaft. The motor is arranged above the purifying assembly and is connected with the purifying assembly to drive the purifying assembly into rotation.

In some examples, the driving device includes a differential assembly which is connected with the motor and is configured to control rotation speeds of different rotating members in the purifying assembly to be different.

Further, the differential assembly includes: an inner output shaft, which is connected with the motor shaft of the motor and configured to rotate around the same axis and at the same speed as the motor shaft; and an outer output shaft, which has a center hole and is arranged around the inner output shaft. The outer output shaft is connected with the inner output shaft through a driving member to make the rotation speed of the inner output shaft different from that of the outer output shaft.

In some examples, the driving member includes a gear set. The gear set includes: a first gear, which is arranged around the inner output shaft and configured to rotate synchronously with the inner output shaft; a second gear, which is engaged with the first gear; and a third gear, which is coaxial with the second gear, and configured to rotate synchronously with the second gear. The outer output shaft is provided with a toothed part, and the third gear is engaged with the toothed part on the outer output shaft.

In some examples, the inner output shaft is connected with one of the rotary disk and the rotary cylinder of the purifying assembly, and the outer output shaft is connected with the other of the rotary disk and the rotary cylinder of the purifying assembly.

According to yet another example of the disclosure, the purifying member includes: a fan, which is arranged above the purifying assembly to drive the air to flow from the air inlet to the air outlet via the purifying assembly. The driving device is connected with the fan to drive the fan into rotation.

In some examples, the water supply member includes: a water tank. The water tank has a water inlet and a water outlet, and the water storage cavity communicating the water inlet with the water outlet is defined in the water tank.

In some examples, the water supply member includes a water collecting part which is arranged between the guide member and the water tank, and is connected with the guide member and the water tank.

In some examples, the water supply member includes a base and a guide rail. The base is supported at the bottom of the water tank, and forms a bottom wall of the accommodating cavity. The guide rail is fixed on the base, and the water tank is slideably arranged on the guide rail.

Further, a bottom of the base is provided with a roller.

In an example, the air purifier further includes an electrolyzing device, which is arranged in the accommodating cavity to purify the liquid in the accommodating cavity.

According to yet another embodiment of the disclosure, the electrolyzing device is arranged in the water storage cavity to purify the liquid in the water storage cavity.

According to yet another embodiment of the disclosure, the electrolyzing device is arranged between the guide member and the water storage cavity, and is in communication with each of the guide member and the water storage cavity.

According to yet another embodiment of the disclosure, the electrolyzing device includes a water collecting shell and an electrode. The water collecting shell is provided with a water inlet hole and a water outlet hole. A water collecting cavity communicating the water inlet hole with the water outlet hole is defined in the water collecting shell. The water collecting cavity is connected with the guide member through the water inlet hole, and is connected with the water storage cavity through the water outlet hole. The electrode is arranged in the water collecting cavity.

According to yet another embodiment of the disclosure, the air moving member includes a support frame, a blower and a filtering member. The support frame is arranged on an inner wall of the accommodating cavity. The upper end of the purifying member is fixed on a lower side of the support frame. The blower is fixed on the support frame. The filtering member is arranged above the blower.

In some examples, the blower is a multi-vane centrifugal blower.

In some examples, the air moving member includes: a second grille arranged at the air outlet.

According to yet another example of the disclosure, the air purifier further includes a watertight structure, which is fixedly connected with the inner wall of the accommodating cavity and is in communication with the water storage cavity. An accommodating space is defined in the watertight structure, and a volume of the accommodating space is greater than the volume of the water storage cavity.

In some examples, the watertight structure includes an accommodating member and a directing member. A flow collecting part is arranged on the accommodating member, and the flow collecting part defines a flow collecting groove. A drainage mouth is arranged in the flow collecting groove. A drainage channel is defined in the directing member, and one end of the drainage channel is in communication with the drainage mouth and another end is in communication with the water storage cavity.

Further, the accommodating member includes a cylindrical body, an upper retainer ring and a lower retainer ring. The cylindrical body is connected with the inner wall of the accommodating cavity. The upper retainer ring is arranged on a upper end of the cylindrical body and shields the gap between an outer circumference of the blower and the inner wall of the accommodating cavity. A support frame is arranged on the upper retainer ring. The lower retainer ring is arranged on a lower end of the cylindrical body, and forms the flow collecting part. An annular accommodating space is defined between the inner wall of the cylindrical body, the flow collecting part and the upper retainer ring.

According to yet another embodiment of the disclosure, a wire access pipe extending in an axial direction is arranged in the accommodating cavity.

According to yet another embodiment of the disclosure, the housing includes: a first housing, a second housing and a third housing which are detachably connected to one another. The first housing is located above the third housing. The second housing is connected between the first housing and the second housing. The air moving member is located in the first housing. The purifying member is located in the second housing. The water supply member is located in the third housing.

Further, the air inlet is arranged on a side wall of the third housing, and an edge of the air inlet is forms a chamfer extending along an air inflow direction.

Additional aspects and advantages of the disclosure will be partly given in the following description, and portion of them will become apparent from the description below or be known through the practice of the disclosure.

BRIEF DESCRIPTION OF THE DRAWINGS

The above and/or additional aspects and advantages of the disclosure will become apparent and be easily understood from the description of embodiments in combination with the accompanying drawings.

LIST OF REFERENCE NUMERALS

Figure 1:
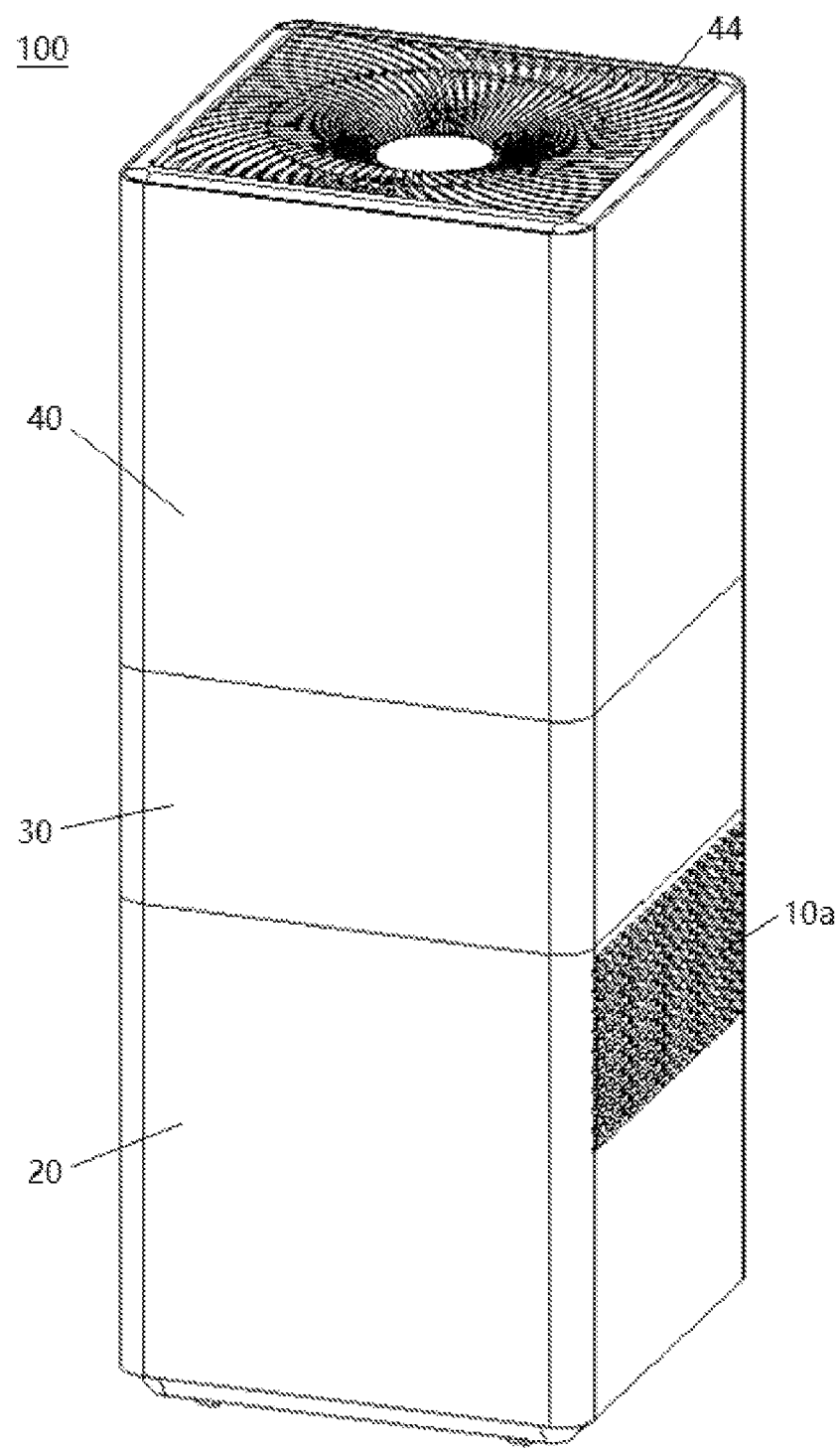
FIG. 1 illustrates a perspective view of an air purifier according to an embodiment of the disclosure.

100: air purifier;
10: housing; 10a: air inlet; 10b: air outlet; 10c: accommodating cavity; 11: first housing; 12: second housing; 13: third housing;
20: water supply member; 20a: water storage cavity; 21: water tank; 22: water collecting part; 221: water collecting groove; 222: center interface; 223: water collecting interface; 23: base; 231: roller; 24: guide rail; 25: connecting pipe; 26: fixing plate; 27: connecting plate;
30: purifying member;
31: purifying assembly; 311: rotary capturing member; 312: rotary purifying member; 313: first rotary disk; 314: second rotary disk; 3134: fourth mesh; 315: first interval space; 316: cylinder; 317: second interval space;
32: water distribution assembly; 321: water inlet pipe; 3211: water discharge end; 322: water driving member; 3221: water conveying member; 3222: connector; 323: partition tube; 3231: a joint part; 323a: lee area; 3223: water pump;
33: driving device; 331: motor; 332: differential assembly; 3321: inner output shaft; 3322: outer output shaft;

3323: toothed part; 3331: first gear; 3332: second gear; 3333: third gear; 3334: first connecting member; 3335: second connecting member; 3336: first bearing; 3337: second bearing; 3338: third bearing; 334: tank;

34: guide member; 341a: water guide groove; 341b: water guide mouth; 3411: annular base plate; 3412: annular baffle; 342: flow guider;

35: first grille;

40: air moving member; 41: support frame; 42: blower; 43: filtering member; 44: second grille; 45: bracket;

50: electrolyzing device; 60: wire access pipe;

70: watertight structure; 70a: accommodating space; 71: accommodating member; 711: flow collecting part; 7111: flow collecting groove; 7112: drainage mouth; 712: cylinder; 713: upper retainer ring; 714: connection portion; 72: directing member.

DETAILED DESCRIPTION

The embodiments of the disclosure are described in detail below. Examples of the embodiments are shown in the accompanying drawings, where the same or similar reference numbers represent from beginning to end the same or similar components or components having the same or similar functions. The embodiments described below by reference to the accompanying drawings are exemplary, and they are intended only to explain the disclosure and are not understood as a limitation to the disclosure.

An air purifier 100 according to the embodiments of the disclosure is described below by reference to FIG. 1 to FIG. 24. The air purifier 100 is configured to purify the air to provide users with a clean and comfortable breathing environment.

An air purifying device in the related technology directly uses a High Efficiency Particulate Air Filter (HEPA) to purify the air. The filter generally captures particulate matters of 5 μm and 10 μm. Dust particles with small volume and high density slow down when passing through the HEPA under the effect of gravity, and naturally settle on the HEPA. A large amount of air swirls are formed due to the unevenly woven filter, small particles are adsorbed on the HEPA under the action of airflow cyclone, and superfine particles do Brownian motion and hit the HEPA fiber layer, and are thus purified under the effect of Van der Waals' force (VDW). But after the filter is used for a period of time, that is, after it captures a certain quality of pollutant particles, its purification capacity will degrade, and as the accumulation of pollutant particles, it will produce peculiar smell, and it is necessary to be replaced regularly, so there is a technical problem of Cumulate Clean Mass (CCM).

For another example, an activated carbon filter sieve is used to filter the air. The activated carbon filter sieve includes particles/powder of activated carbons and chemical agents impregnated on the activated carbon filter sieve, a frame and a filter sieve. The chemical agents and the activated carbons impregnated on activated carbon filter sieve remove gaseous pollutants in the air respectively through chemical adsorption and physical adsorption. After the filter adsorbs a certain quality of formaldehyde, and after the chemical agents impregnated on the activated carbon filter sieve loses efficacy, the activated carbons come to saturation and produce peculiar smell, so there are also technical problems of regular replacement and CCM.

Compared with the air purifying devices in the related technologies, the air purifier 100 in the embodiments of the disclosure may purify the air continuously, circularly and efficiently, so the degradation of purification efficiency due to the accumulation of pollutants in the air purifier 100 is effectively avoided, and there is no need for regular replacement, which not only provides users with a clean and comfortable breathing environment, but also brings great convenience for use.

As shown in FIG. 1 to FIG. 4, the air purifier 100 according to the embodiments of the disclosure includes a housing 10, a water supply member 20, a purifying member 30 and an air moving member 40. The purifying member 30 includes a purifying assembly 31, a water distribution assembly 32 and a driving device 33.

Specifically, the housing 10 is provided with an air inlet 10a and an air outlet 10b. The air inlet 10a is arranged on the side wall of the housing 10. The housing 10 defines an accommodating cavity 10c. The accommodating cavity 10c is in communication with the air inlet 10a and the air outlet 10b. The water supply member 20 is located in the accommodating cavity 10c. A water storage cavity 20a is defined in the water supply member 20 for storing liquid like water. The purifying member 30 is also arranged in the accommodating cavity 10c. The purifying member 30 is located above the water supply member 20 and purifies the air in the accommodating cavity 10c. The air moving member 40 is also arranged in the accommodating cavity 10c. The air moving member 40 is located above the purifying member 30. The air moving member 40 provides power for driving the airflow, so that the airflow enters the accommodating cavity 10c from the air inlet 10a and flows upwards, and after purified by the purifying member 30, the airflow is discharged from the air outlet 10b.

Further, the purifying assembly 31 is in the accommodating cavity 10c, the driving device 33 is located above the purifying assembly 31. The driving device 33 is connected with the purifying assembly 31, and is configured to drive the purifying assembly 31 into rotation in the accommodating cavity 10c. The water distribution assembly 32 is configured to guide the water in the water storage cavity 20a upwards, so that the water storage cavity 20a flows upwards and distributes water towards the purifying assembly 31.

In some example of the disclosure, the water distribution assembly 32 distributes water towards the interior of the purifying assembly 31. After the water enters the purifying assembly 31, the purifying assembly 31 rotating at a high speed may tear the water into small droplets, and the droplets may capture pollutants (including gaseous, liquids and solid particle pollutants) in the airflow when the droplets are thrown towards the inner wall of the accommodating cavity 10c under the action of centrifugal force. A portion of the droplets carrying the dust are thrown onto the inner wall of the accommodating cavity 10c to capture the pollutants in the airflow, which takes an effect of purifying the airflow. On the other hand, the purifying assembly 31 may also capture the droplets in the airflow and throw the droplets towards the inner wall of the accommodating cavity 10c, the water accumulates on the inner wall of the accommodating cavity 10c and slides down to achieve a gas-liquid separation effect, that is, the purifying assembly 31 in the embodiment has dual effects of capturing the pollutants in the airflow and separating gas and liquid.

In some other example of the disclosure, when the water distribution assembly 32 distributes water to the purifying assembly 31, the droplets sprayed from the water distribution assembly 32 may capture the pollutants (including gaseous, liquids and solid particle pollutants) in the airflow to achieve the effect of purifying the airflow. During the airflow drives the droplets carrying the carrying the dust to continue to flow upwards, the purifying assembly 31 rotating at a high speed captures the droplets in the airflow, and throws the droplets onto the inner wall of the accommodating cavity 10c. The water accumulates on the inner wall of the accommodating cavity 10c and slides down along the inner wall of the accommodating cavity 10c to achieve the gas-liquid separation effect, that is, in these examples, the purifying assembly 31 has only the gas-liquid separation effect.

The air purifier 100 according to the embodiments of the disclosure provides, through the air moving member 40, power for driving the airflow to flow upwards. The driving device 33 provides power for driving the purifying assembly 31 to rotate. In this way, the purifying assembly 31 can continuously and efficiently purify the pollutants in the air without attenuation, thereby providing users with a comfortable and clean breathing environment. The number of times of replacing a filter sieve in the air moving member is fewer, even it is not necessary to replace the filter sieve regularly, but only need to replace the water in the water storage cavity 10b regularly, so it is easy to use and the cost is reduced. Moreover, the air purifier 100 is compact in structure and significant in effect of purifying the air, and has the advantages of small volume, low pressure loss, low energy consumption and high efficiency.

According to an embodiment of the disclosure, the purifying assembly 31 includes a rotary capturing member 311 and a rotary purifying member 312. The rotary capturing member 311 is located above the rotary purifying member 312. The rotary capturing member 311 rotates at a high speed in the accommodating cavity 10c, and the rotary purifying member 312 also rotates at a high speed in the accommodating cavity 10c. The rotary purifying member 312 is spaced apart from the side wall of the housing 10 in the radial direction.

In an example, the rotary purifying member 312 is a rotating packing bed of annular shape, in which an annular space is defined, and the air inlet 10a is at the same axial height as the rotating packing bed. The rotary capturing member 311 is arranged above the rotating packing bed, and the rotary capturing member 311 includes a cylinder 316 and a rotary disk 316. The outer circumferential wall of the cylinder 316 is a cylindrical surface. The cylinder 316 is spaced apart from the inner side wall of the housing 10. The rotary disk is arranged above the cylinder 316, and a mesh for passage of the airflow is arranged on at least the portion of the rotary disk between the cylinder 316 and the housing 10 in the radial direction.

When the water distribution assembly 32 distributes water towards the rotating packing bed, water is sprayed into the annular space of the rotating packing bed and then into the rotating packing bed where the water is torn into a aqueous stream formed by droplets, liquid membrane, and liquid flow, at the same time, the airflow entering the rotating packing bed from the air inlet 10a moves in the direction opposite to that of the aqueous stream. When the rotating packing bed rotates at a high speed, the water is thrown out under the action of centrifugal force onto the inner wall of the accommodating cavity 10c, and the water accumulates on the inner wall of the accommodating cavity 10c and flows to the water storage cavity 20a. The purified airflow carrying portion of the droplets flows towards the air outlet 10b.

For example, the packing in the rotating packing bed may be porous packing made of plastic, ceramic or metal, and may also be porous disc packing and corrugated plate packing, etc. In some embodiments, the water distribution assembly 32 may be fixed, and the rotating packing bed rotates at high speed relative to the water distribution assembly 32 to facilitate conveying water through the water distribution assembly 32.

The rotary capturing member 311 is arranged above the rotating packing bed. The airflow may be first purified by the rotating packing bed and then flow through the rotary capturing member 311. The rotary capturing member 311 includes the cylinder 316 and the rotary disk. The outer circumferential wall of the cylinder 316 is a cylindrical surface, which means that the outer circumferential wall of the cylinder 316 is not provided with holes or grooves, for example, the inside of the cylinder 316 is not in communication with the outside of the cylinder 316, and the outer circumferential wall of the cylinder 316 may be an airtight and watertight structure.

The cylinder 316 is spaced apart from the inner side wall of the housing 10. The rotary disk is arranged on the upper side of the cylinder 316, and a mesh for passage of the air is arranged on at least the portion of the rotary disk between the cylinder 316 and the housing 10 in a radial direction. Because the driving device 33 may drive the rotary purifying member 312 and the rotary capturing member 311 to rotate synchronously, the airflow purified by the rotating packing bed flows towards the air outlet 10b carrying portion of the droplets, and the droplets in the airflow may be captured by the rotary disk, so that the droplets are thrown to the inner wall of the housing 10 under the action of centrifugal force, and slide along the inner wall of the housing 10 to the rotating packing bed. In this way, the droplets are prevented from escaping, and the clean airflow after purification may flow out from the air outlet 10b through the mesh for passage of the air.

Figure 4:
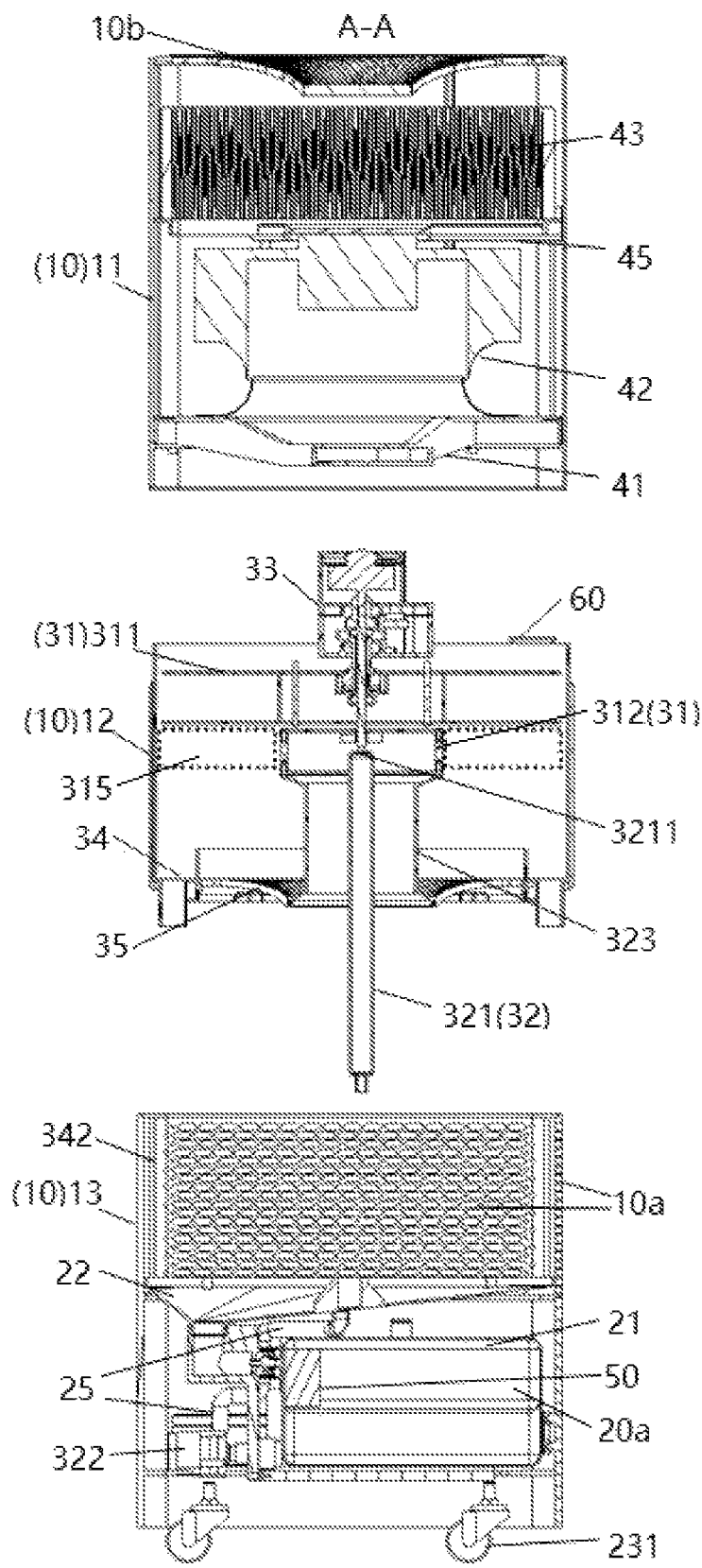
FIG. 4 illustrates a sectional view along the line A-A in FIG. 3.

As shown in FIG. 4, according to an example of the disclosure, the rotary capturing member 311 is in the form of a rotary disk, and the rotary purifying member 312 is in the form of a rotary cylinder, a first mesh is arranged on the side wall of the rotary cylinder, a first interval space 315 is defined between the rotary cylinder and the inner wall of the housing 10, and a second mesh is arranged on at least the part, facing the first interval space 315 in the radial direction, of the rotary disk.

Specifically, the air inlet 10a is arranged on the side wall of the housing 10, and the air inlet 10a is located below the purifying assembly 31. The water distribution assembly 32 distributes water to the rotary cylinder. After the water is sprayed into the rotary cylinder, the rotary cylinder rotating at a high speed tears the water into tiny droplets through the first mesh. Under the action of centrifugal force, the tiny droplets are thrown into the first interval space 315, at this point, the tiny droplets in the first interval space 315 may capture impurity particles in the airflow, portion of the dust carrying droplets are thrown onto the inner wall of the accommodating cavity 10c, the droplets in the airflow captured by the rotary disk are also thrown onto the inner wall of the accommodating cavity 10c, the water accumulates on the inner wall of the accommodating cavity 10c and slides down, and the clean airflow flows through the second mesh towards the air outlet 10b and keeps flowing upwards through the second mesh.

As shown in FIG. 4, according to an example of the disclosure, the purifying assembly 31 includes multiple stages, and each stage of the purifying assembly 31 includes the rotary capturing member 311 and the rotary purifying member 312. The multiple stages of the purifying assembly 31 are successively connected to one another in an airflow direction. The airflow enters the accommodating cavity 10c from the air inlet 10a and flows through the multiple stages of the purifying member 31 in turn from the bottom to the top. Through purification effects of the multiple stages of the purifying member 31, a better purification and gas-liquid separation effect may be achieved, thus further ensuring the airflow clean.

In some examples, the purifying assembly 31 may be configured to further purify the air that has been preliminarily purified, and may reduce moisture of the air. The purifying assembly 31 is arranged in the accommodating cavity 10c and between the air inlet 10a and the air outlet 10b. The droplets in the air may be captured by the purifying assembly 31, and in this process, the contact between the droplets and dust particles in the air can also be intensified, which can not only reduce the moisture of the air, but also improve the purification effect.

Figure 6:
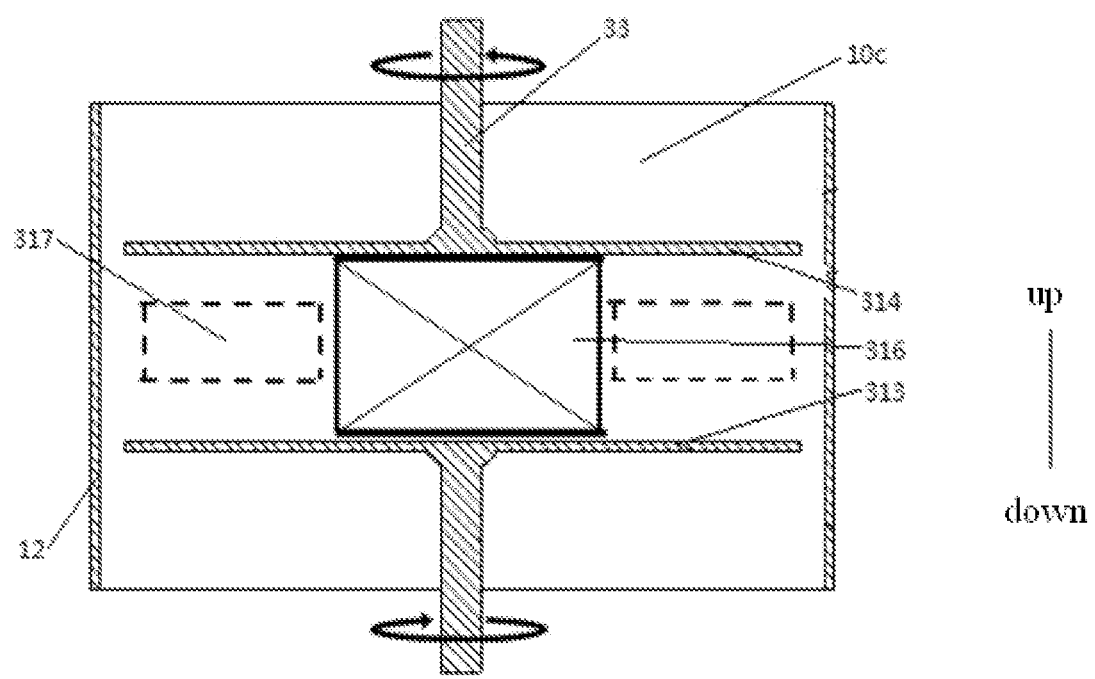
FIG. 6 illustrates a schematic diagram of a purifying assembly of an air purifier according to an embodiment of the disclosure.

Further, as shown in FIG. 6, the purifying assembly 31 includes the rotary disk provided with the mesh and the cylinder 316. The rotary disk includes a first rotary disk 313 and a second rotary disk 314. The first rotary disk 313 and the second rotary disk 314 can be both rotatably arranged in the accommodating cavity 10c, and the rotating direction of the first rotary disk 313 is opposite to that of the second rotary disk 314. For example, the first rotary disk 313 may rotate in a clockwise direction, and the second rotary disk 314 rotates in a counterclockwise direction; or, the first rotary disk 313 rotates in the counterclockwise direction, and the second rotary disk 314 rotates in the clockwise direction.

Figure 7:
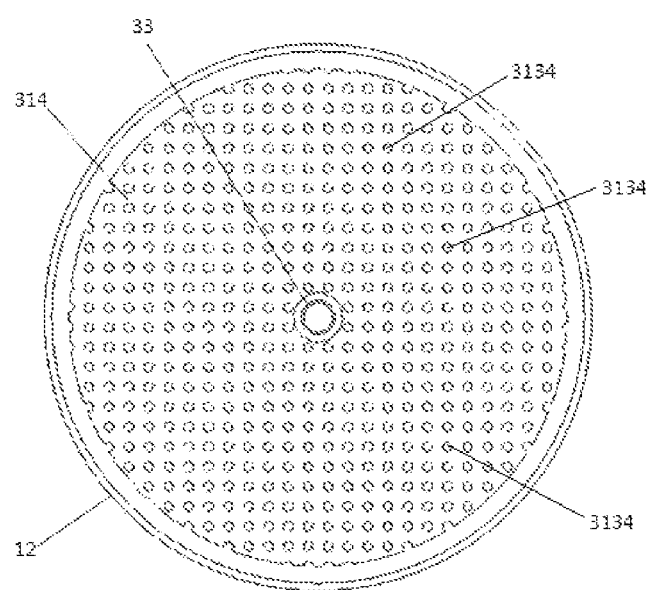
FIG. 7 illustrates a top view of a purifying assembly as illustrated in FIG. 6.

As shown in FIG. 7, the first rotary disk 313 is provided with a third mesh, the second rotary disk 314 is provided with a fourth mesh, the second rotary disk 314 is arranged above the first rotary disk 313, and the second rotary disk 314 is spaced apart from the first rotary disk 313; that is, in the direction where the air flows from the air inlet 10a to the air outlet 10b, the first rotary disk 313 and the second rotary disk 314 are sequentially arranged, and the air flows through the first rotary disk 313 and the second rotary disk 314 in turn.

The air may be preliminarily captured by the first rotary disk 313, so as to capture portion of the droplets in the air. Specifically, the air preliminarily captured flows to the first rotary disk 313; because the first rotary disk 313 rotates at a high speed, and a shear force generated by the high-speed rotation of the first rotary disk 313 may drive the air to generate a centrifugal motion, and before the air touches the first rotary disk 313, portion of the droplets in the air may be spaced apart from the air. After the preliminary purification, the relatively small droplets contained in the air continue to flow with the air and flow to the first rotary disk 313. When the air flows through the first rotary disk 313, the droplets in the air touch the first rotary disk 313. The droplets may be spread into a thin liquid membrane or atomized into tiny droplets on the first rotary disk 313 with multiple third meshes, and the thin liquid membrane or the atomized tiny droplets collide strongly with the air passing through a gap of the first rotary disk 313, thus further increasing an air-liquid contact area; at the same time, the spread liquid membrane may also capture the dust particles in the air more efficiently, so as to further strengthen dust removal. At the same time, the first rotary disk 313 may also drive the air to keep flowing upwards, thus improving the liquidity.

The first rotary disk 313 and the second rotary disk 314 are arranged apart in the direction of air flow. The air preliminarily purified and captured by the first rotary disk 313 flows between the first rotary disk 313 and the second rotary disk 314. Because the first rotary disk 313 and the second rotary disk 314 rotate in the opposite directions with respect to one another, the shear forces generated by the first rotary disk 313 and the second rotary disk 314 are opposite, and the air is subjected to opposite forces when flowing between the first rotary disk 313 and the second rotary disk 314, as a result, a circumferential motion of the air in the interval space generates a certain counteracting effect, and thus a circumferential motion velocity of the air is reduced. The density of the droplets carried in the air is larger, and the inertia effect is larger than that of gas, so the motion of the droplet changes less than that of the air, that is, due to the inertia effect, the droplets in the air will keep doing centrifugal motion, and the inertia effect of gas is relatively small compared to the liquid, so the gas and liquid are more easily separated, which improves the gas-liquid separation effect.

The air keeps flowing to the second rotary disk 314, and the second rotary disk 314 may further capture the air to capture the liquid in the air, thus achieving multistage separation. In this way, not only the purification effect may be improved, but the second rotary disk 314 may also accelerate the captured air to make it do the centrifugal motion, so as to improve the purification effect, and provide power for the air to flow to the air outlet 10b. The principle of purifying air and capturing droplet of the second rotary disk 314 is the same as that of the first rotary disk 313, so it will not be repeated here.

The cylinder 316 is arranged between the first rotary disk 313 and the second rotary disk 314. The outer circumferential wall of the cylinder 316 is the cylindrical surface and is spaced apart from the side wall of the housing 10. That is, the outer circumferential wall of the cylinder 316 is formed into a closed wall surface, and the inside of the cylinder 316 is not in communication with the outside of the cylinder 316, for example, the cylinder 316 may be formed into an airtight and watertight structure. As shown in FIG. 1, the cylinder 316 is spaced apart from the side wall of the housing 10 to define a second interval space 317, and the air may flow in the second interval space 317. Because the separation effect is poor due to a small circumferential velocity of the air in a central axis area of the first rotary disk 313 and the second rotary disk 314, the cylinder 316 may be arranged to prevent the air from flowing through the area near the central axis of the first rotary disk 313 and the second rotary disk 314, thus improving the gas-liquid separation effect and then improving the purification effect. It is understandable that the cylinder 316 may be connected with the first rotary disk 314 or the second rotary disk 314, in which case the cylinder 316 rotates synchronously with the first rotary disk 314 or the second rotary disk 314, and the cylinder 316 may also be connected to the inner wall of the accommodating cavity 10c to stay fixed, which is not specified in the disclosure.

The air preliminarily purified may be further purified by the purifying assembly 31 according to the embodiments of the disclosure, so that the air flowing out from the air outlet 10b is cleaner. Because the first rotary disk 313 and the second rotary disk 314 rotate in opposite directions with respect to one another, and shear actions are opposite, the air is subjected to forces in different directions when flowing between the first rotary disk 313 and the second rotary disk 314, thus reducing the circumferential motion velocity of the air. The droplets carried in the air keep doing the centrifugal motion due to its high density and the inertia effect that is larger than that of the gas, while the inertia effect of the gas is smaller than that of the liquid, it is easier for the droplets to be separated. Thus, a capturing device for air purification is simple in structure and has a good air purification effect.

According to another embodiment of the disclosure, the water distribution assembly 32 is arranged below the purifying assembly 31. The water distribution assembly 32 includes a water inlet pipe 321 and a water driving member 322. In some examples of the disclosure, a water discharge end 3211 of the water inlet pipe 321 is provided with a plurality of water injection nozzles, the water discharge end 3211 of the water inlet pipe 321 extends into the purifying assembly 31, and the water flowing upward along the water inlet pipe 321 is circumferentially sprayed into the purifying assembly 31 through the water injection nozzle. In some other examples of the disclosure, the water discharge end 3211 of the water inlet pipe 321 is in the form of an atomizing nozzle. The water discharge end 3211 of the water inlet pipe 321 may extend into the purifying assembly 31. The water is sprayed into the purifying assembly 31 through the atomizing nozzle. The water discharge end 3211 of the water inlet pipe 321 may also be located below the purifying assembly 31. The water is sprayed after being atomized by the atomizing nozzle, and the sprayed atomized droplets capture the pollutants in the airflow, at this point, the purifying assembly 31 takes the gas-liquid separation effect. The water driving member 322 is connected with the water inlet pipe 321 to provide power for the water flowing upwards along the water inlet pipe 321, thus continuously driving the water in the water storage cavity 20a to flow upwards.

In some examples, the water discharge end 3211 of the water inlet pipe 321 is located below the purifying assembly 31, and the water discharge end 3211 of the water inlet pipe 321 and the purifying assembly 31 are arranged apart in the vertical direction; for example, the water inlet pipe 321 is located directly below the purifying assembly 31, the water discharge end 3211 of the water inlet pipe 321 is in the form of the atomizing nozzle, and the water is directly sprayed out in all directions through the atomizing nozzle. When the water is atomized, it forms droplets that can capture the pollutants in the airflow to achieve the airflow purification effect. The purifying assembly 31 may capture the droplets containing pollutants carried the airflow and throw the droplets onto the inner wall of the accommodating cavity 10c to achieve the gas-liquid separation effect. The number of structural parts in the embodiment is small and the overall structure is simple.

Figure 8:
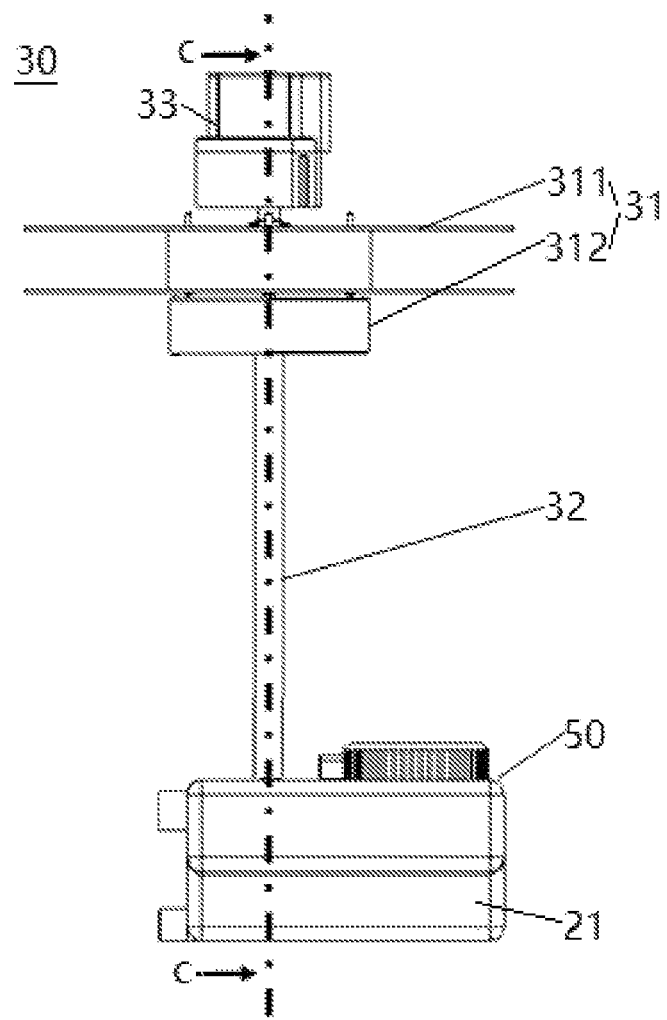
FIG. 8 illustrates a schematic diagram of a purifying member and a water supply member of an air purifier according to an embodiment of the disclosure.
Figure 9:
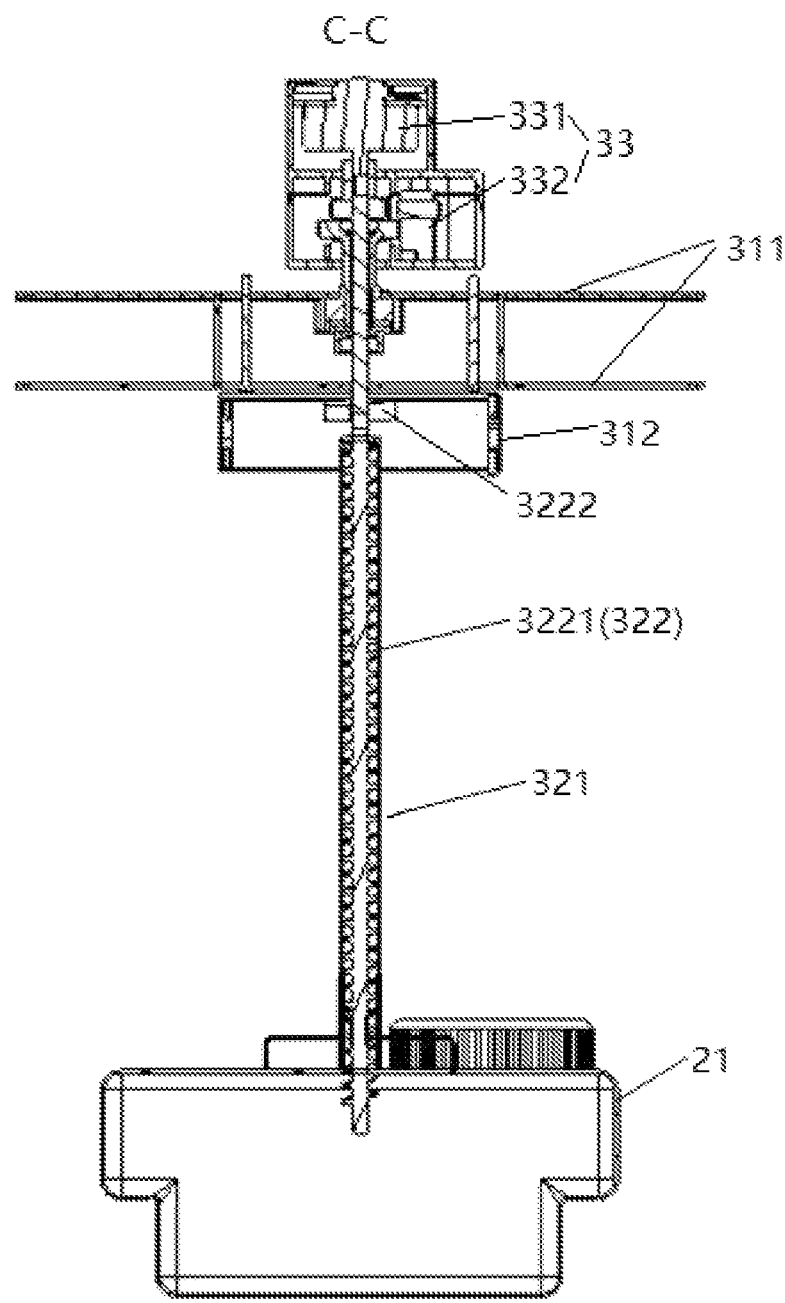
FIG. 9 illustrates a sectional view along the line C-C in FIG. 8.

As shown in FIG. 8 and FIG. 9, in some examples, the water driving member 322 includes a water conveying member 3221 and a connector 3222. The water conveying member 3221 is movably arranged in the water inlet pipe 321 to convey liquid upwards, and may drive water to flow upwards along the inner wall of the water inlet pipe 321. The water conveying member 3221 is connected with the purifying assembly 31 through the connector 3222, for example, the upper end of the water conveying member 3221 is connected with the rotary cylinder of the purifying assembly 31, so that the water conveying member 3221 may rotate synchronously with the rotary cylinder. In this way, the water at the lower end of the water inlet pipe 321 is guided upwards along its inner wall to the water discharge end 3211. By arranging the water conveying member 3221 in the water inlet pipe 321 and using the water conveying member 3221 to convey liquid upwards, there is no need to set a water pump 3223 at the water inflow end of the water inlet pipe 321, which makes the structure more compact and saves the operation cost.

In an example, the water conveying member 3221 is a screw. The screw is configured to rotate synchronously with the purifying assembly 31 (for example, the rotary cylinder) in the water inlet pipe 321, so that the rotation of the screw can be driven by the high-speed rotation of the rotary cylinder. A conveying space is defined between the screw and the water inlet pipe 321, and the screw may press the water in the water storage cavity 20a into the conveying space to convey the water upwards. The screw spirally rotates in the water inlet pipe 321 to guide the water in the water storage cavity 20a to flow upwards, so as to convey liquid from bottom to top, which eliminates the need for a water pump 3223 in the related technology and makes the structure more compact. At the same time, the screw may be rotationally driven by the rotary cylinder of the purifying assembly 31, which reduces the operating cost.

In an example, the water driving member 322 may also be the water pump 3223. The water pump 3223 is connected with the water inflow end of the water inlet pipe 321. The water pump 3223 may drive the water in the water storage cavity 20a to flow upwards to the water discharge end 3211, that is, the water pump 3223 provides power for water to flow upwards along the water inlet pipe 321.

As shown in FIG. 10 to FIG. 15, according to another example of the disclosure, the water distribution assembly 32 includes a partition tube 323. The partition tube 323 is located below the purifying assembly 31, is arranged around the periphery of the water inlet pipe 321, and is coaxial with and spaced apart from the water inlet pipe 321. A lee area 323a is defined between the water inlet pipe 321 and the partition tube 323, which may effectively prevent the airflow from the air inlet 10a from entering the lee area 323a and flowing upwards when the airflow flows upwards, and enables the airflow to flow to the air outlet 10b along the outside of the partition tube 323 shown in FIG. 10, that is, the airflow flows upwards along the outside of the partition tube 323 to prevent influence on the effect of spraying water or atomizing of the water inlet pipe 321.

Figure 11:
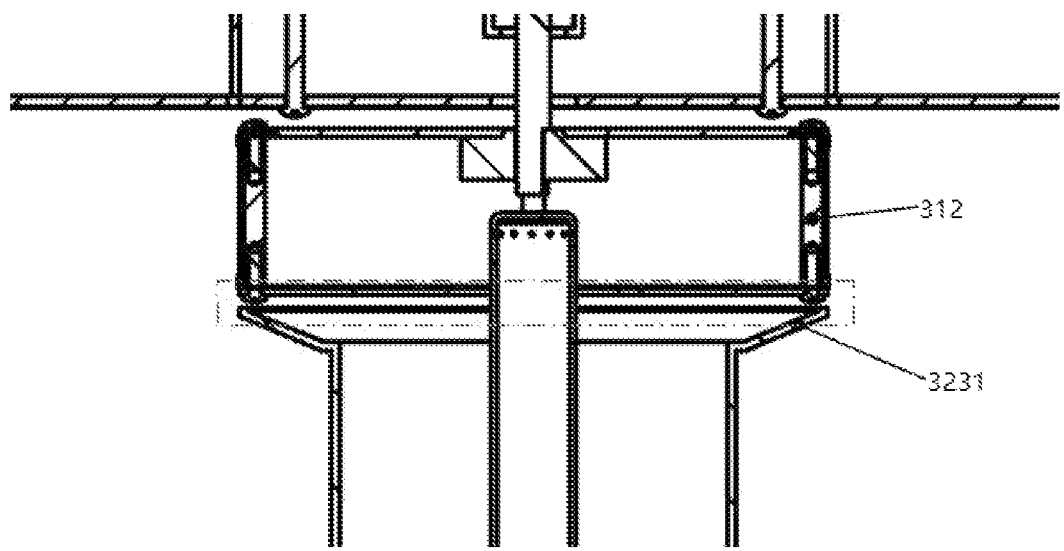
FIG. 11 illustrates a partial schematic diagram in FIG. 10.

As shown in FIG. 11, the upper end of the partition tube 323 is provided with a joint part 3231. The lower end of the joint part 3231 is connected with the partition tube 323, and the upper end of the joint part 3231 is spaced apart from the rotary cylinder of the purifying assembly 31 in the axial direction, so as to prevent the rotary cylinder from touching the partition tube 323 during rotation. And the radial dimension of the upper opening of the joint part 3231 is equal to that of the rotary cylinder, which may prevent the airflow from entering the lee area 323a. The cross section of the joint part 3231 is tapered, which has a good joint effect on the partition tube 323 and the purifying assembly 31.

Figure 12:
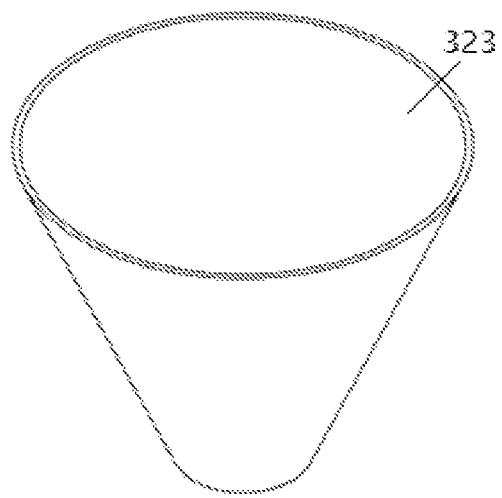
FIG. 12 illustrates a perspective view of a partition tube of an air purifier according to an embodiment of the disclosure.
Figure 13:
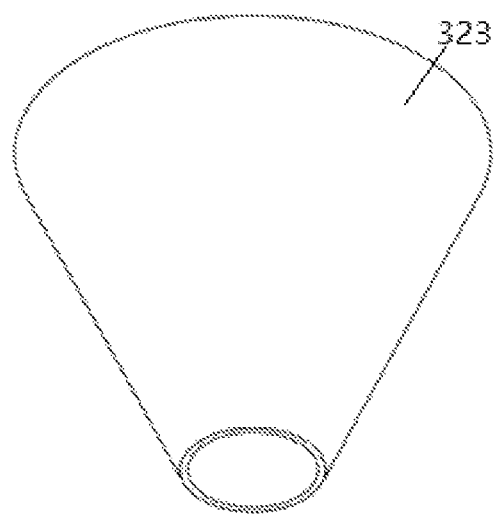
FIG. 13 illustrates a perspective view of another perspective of a partition tube of an air purifier according to an embodiment of the disclosure.
Figure 14:
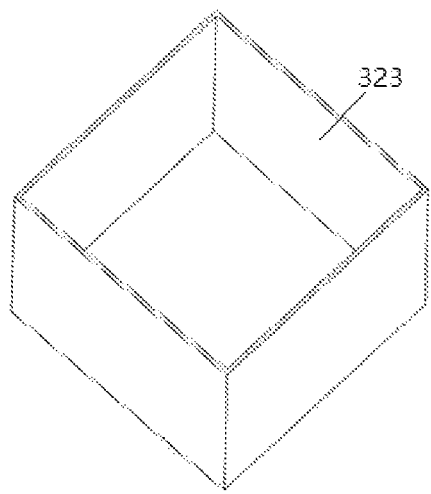
FIG. 14 illustrates a perspective view of a partition tube of an air purifier according to another embodiment of the disclosure.
Figure 15:
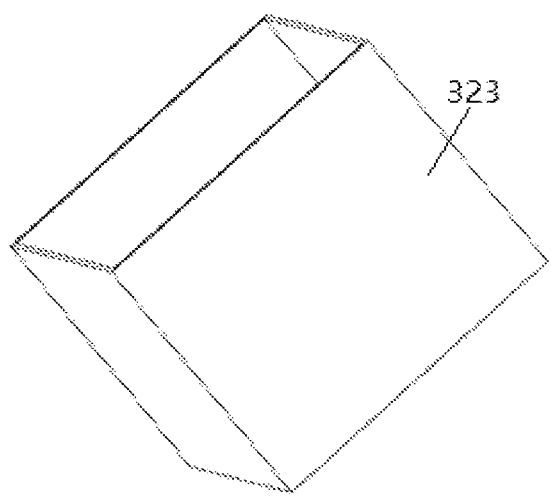
FIG. 15 illustrates a perspective view of another perspective of a partition tube of an air purifier according to another embodiment of the disclosure.

In an example, the partition tube 323 may also be formed into a tapered structure (as shown in FIG. 12 and FIG. 13) and a square structure (as shown in FIGS. 14 and 15), which can prevent the airflow from entering the rotary cylinder along the water inlet pipe 321. It is to be noted that the upper end of the partition tube 323 is spaced apart from the rotary cylinder of the purifying assembly 31 in the axial direction, for example, a narrow slit is formed between the upper end of the partition tube 323 and the rotary cylinder of the purifying assembly 31, which can not only prevent the airflow from entering the rotary cylinder to affect a spraying state, but also avoid a direct contact between the partition tube 323 and the rotary cylinder.

Thus, the liquid is sprayed from the water injection nozzle of the water discharge end 3211 of the water inlet pipe 321 into the area defined by the rotary cylinder of the purifying assembly 31. The partition tube 323 is sheathed outside the water inlet pipe 321, which may avoid the non-uniform spraying caused by the airflow entering the rotary cylinder to disturb the spraying state of the liquid, and further prevent influence on the uniformity of distribution of the liquid in the first interval space 315 after being torn and the equality of size of the droplet particles.

Figure 5:
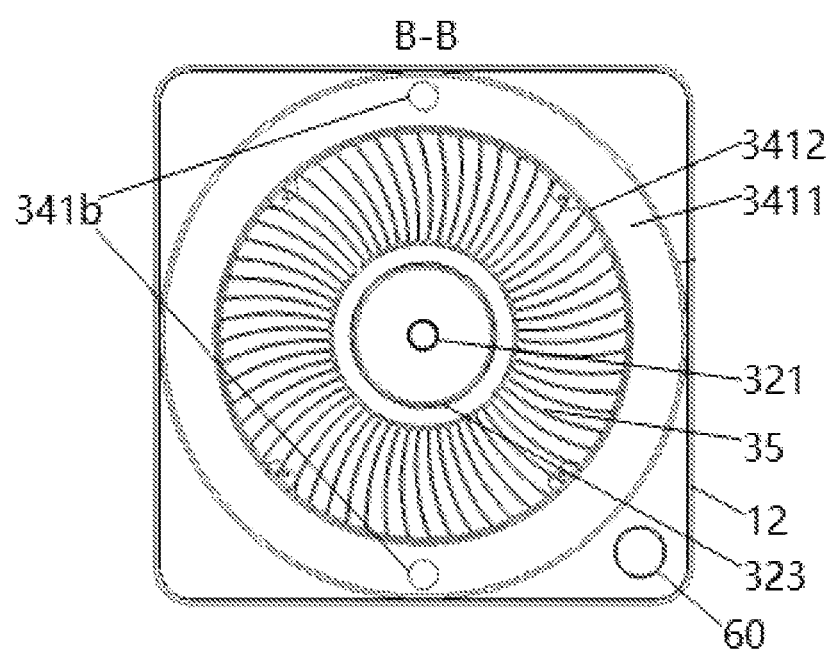
FIG. 5 illustrates a sectional view along the line B-B in FIG. 3.

As shown in FIG. 4 and FIG. 5, according to another embodiment of the disclosure, the guide member 34 is arranged below the purifying assembly 31 along the circumferential direction of the housing 10. It is understandable that in the above embodiment, the accumulated water on the inner wall of the accommodating cavity 10c slides down along the inner wall, so by arranging the drainage component 34 below the purifying assembly 31 in the circumferential direction, the water sliding down from the inner wall of the accommodating cavity 10c may be collected in the circumferential direction, and at the same time, the guide member 34 may guide the water towards the water supply member 20; for example, the water in the guide member 34 is guided towards the bottom of the accommodating cavity 10c, so that the water thrown onto the circumferential wall of the accommodating cavity 10c may be collected to ensure the recycling of water resources.

As shown in FIG. 4 and FIG. 5, the guide member 34 further includes an annular water guide part and a flow guider 342. The air inlet 10a is located below the purifying assembly 31. The annular water guide part is arranged between the purifying assembly 31 and the air inlet 10a. The annular water guide part and the inner wall of the accommodating cavity 10c define a water guide groove 341a. A water guide mouth 341b is arranged on the water guide groove 341a. The water may be guided out of the water guide groove 341a through the water guide mouth 341b in communication with the water guide groove 341a. In this way, the annular water guide part may collect water in the circumferential direction, and by means of the water guide groove 341a arranged between the purifying assembly 31 and the water inlet 10a in the circumferential direction of the inner wall of the accommodating cavity 10c, compared with the air purifying device in the related technology, the water sliding down may be collected in the circumferential direction of the inner wall of the accommodating cavity 10c, and accommodated in the water guide groove 341a, so as to prevent the water from sliding down to the air inlet 10a and spilling out of the air inlet 10a.

The flow guider 342 axially extends along the inner wall of the accommodating cavity 10c. The flow guider 342 is arranged on the inner wall of the accommodating cavity 10c. A flow guide channel is defined between the flow guider 342 and the inner wall of the accommodating cavity 10c, and the flow guide channel is in communication with the water guide mouth 341b. As shown in FIG. 4, the flow guider 342 extends vertically on the inner wall of the accommodating cavity 10c. There are multiple air inlets 10a arranged at intervals on the side wall of the housing 10. The multiple air inlets 10a are separated into multiple groups of air inlets 10a, each group of air inlets 10a includes portion of the multiple air inlets 10a, and the multiple groups of air inlets 10a are arranged at intervals. The flow guider 342 is arranged between two adjacent groups of air inlets 10a. The flow guide channel is in communication with the water guide mouth 341b.

Thus, because the water guide groove 341a is arranged on the upper end of the air inlet 10a, after the water is collected in the water guide groove 341a, the water in the water guide groove 341a is drained from the water guide mouth 341b into the accommodating cavity 10c through the flow guider 342; in this way, the water slides into the water guide groove 341a and then flows down along the flow guide channel through the water guide mouth 341b, so the water does not flow through the air inlet 10a, which prevents the water from spilling out of the air inlet 10a and also avoids the waste of water.

Further, the annular water guide part includes an annular base plate 3411 and an annular baffle 3412. The annular baffle 3412 is connected with the annular base plate 3411 in the circumferential direction and is spaced apart from the inner wall of the accommodating cavity 10c in the radial direction. The inner wall of the accommodating cavity 10c, the annular base plate 3411 and the annular baffle 3412 jointly define the water guide groove 341a. As shown in FIG. 4 and FIG. 5, the water guide groove 341a is an annular groove among the inner wall of the accommodating cavity 10c, the annular base plate 3411 and the annular baffle 3412. The annular baffle 3412 forms the inner ring sidewall of the water guide groove 341a, the inner wall of the accommodating cavity 10c and the corresponding part of the annular baffle 3412 form the outer ring sidewall of the water guide groove 341a, and the annular base plate 3411 forms the bottom wall of the water guide groove 341a. The water sliding down may be collected in the circumferential direction of the inner wall of the accommodating cavity 10c, and accommodated in the water guide groove 341a, which prevents the water from sliding down to the air inlet 10a and spilling out of the air inlet 10a.

According to another embodiment of the disclosure, the purifying member 30 includes a photocatalyst layer. The photocatalyst layer is arranged on the surface of the purifying member 30 and/or the inner wall surface of the accommodating cavity 10c, that is, the photocatalyst layer may be arranged on either the inner wall of the accommodating cavity 10c or the surface (including the surface of the purifying assembly 31 and the water of the water distribution assembly 32) of the purifying member 30; certainly, the photocatalyst layer may also be arranged on both the inner wall of the accommodating cavity 10c and the surface of the purifying member 30. The photocatalyst layer may catalyze the degradation of toxic and harmful gases in the air after being exposed to light, and may also effectively kill a variety of bacteria in the air and decompose and innocuously treat the toxins released by bacteria or fungi, that is, the photocatalyst layer has the function of removing formaldehyde in the air and sterilizing under the irradiation of light.

In an example, the photocatalyst layer may be arranged on the inner wall of the accommodating cavity 10c. Specifically, the photocatalyst layer may be arranged on either the whole inner wall of the accommodating cavity 10c, or portion of the inner wall of the accommodating cavity 10c. In an example, the photocatalyst layer may also be arranged on the surface of the water distribution assembly 32. Specifically, the photocatalyst layer may be arranged on either the whole outer sidewall of the water distribution assembly 32, or portion of the outer sidewall of the water distribution assembly 32.

Preferably, the photocatalyst layer is arranged on the surface of the purifying assembly 31. When rotating at a high speed in the accommodating cavity 10c, the purifying assembly 31 may effectively contact with polluting gas molecules contained in the airflow as well as bacteria, fungi and viruses, and may degrade toxic and harmful gases in the air and disinfect the air when exposed to light. To further improve the air purification effect, the photocatalyst layer may also be arranged on the surface of the purifying assembly 31, the surface of the water distribution assembly 32 and the inner wall of the accommodating cavity 10c.

Thus, by arranging the photocatalyst layer on the inner wall of the accommodating cavity 10c and/or the surface of the purifying member 30, when light is shone on the inner wall of the accommodating cavity 10c and/or the surface of the purifying member 30, the photocatalyst layer cannot only remove particulate matter in the air, but also decompose toxic and harmful gases like formaldehyde in the air. Besides, the photocatalyst layer also has functions of deodorization and sterilization, which significantly improves the air purification effect.

In some examples, the purifying member 30 includes a sterilizing lamp, which is arranged in the accommodating cavity 10c, and for example, the sterilizing lamp may be a Ultra-Violet (UV) lamp. In this way, by providing lighting conditions in the accommodating cavity 10c, the illumination on the inner wall of the accommodating cavity 10c and the surface of the purifying member 30 is more sufficient, and the scope of illumination is expanded, so that the photocatalyst layer can work more efficiently, degrade the toxic and harmful gases in the air more effectively, and remove the bacteria in the air. Moreover, the UV lamp also has a bactericidal effect, so the air purification effect is further strengthen.

Further, the sterilizing lamp may be arranged between the purifying assembly 31 and the water distribution assembly 32. The sterilizing lamp may also be arranged above the purifying assembly 31. The sterilizing lamp may also be arranged between the rotary disk and the rotary cylinder of the purifying assembly 31. The disclosure does not specify the specific position of the sterilizing lamp, as long as it can meet the effect of degrading toxic and harmful gases in the air.

According to yet another embodiment of the disclosure, the portion of the side wall of the housing 10, radially facing the purifying member 30, forms a transparent part. In this way, external visible light can illuminate the photocatalyst layer on the surface of the purifying member 30 through the transparent part, or illuminate the photocatalyst layer on the inner wall of the accommodating cavity 10c, so as to purify the harmful gases like formaldehyde in the air. By arranging the transparent part on the side wall of the housing 10, an external light source of visible light can be used, which saves cost and makes rational use of energy, and the structure is more simple.

Figure 10:
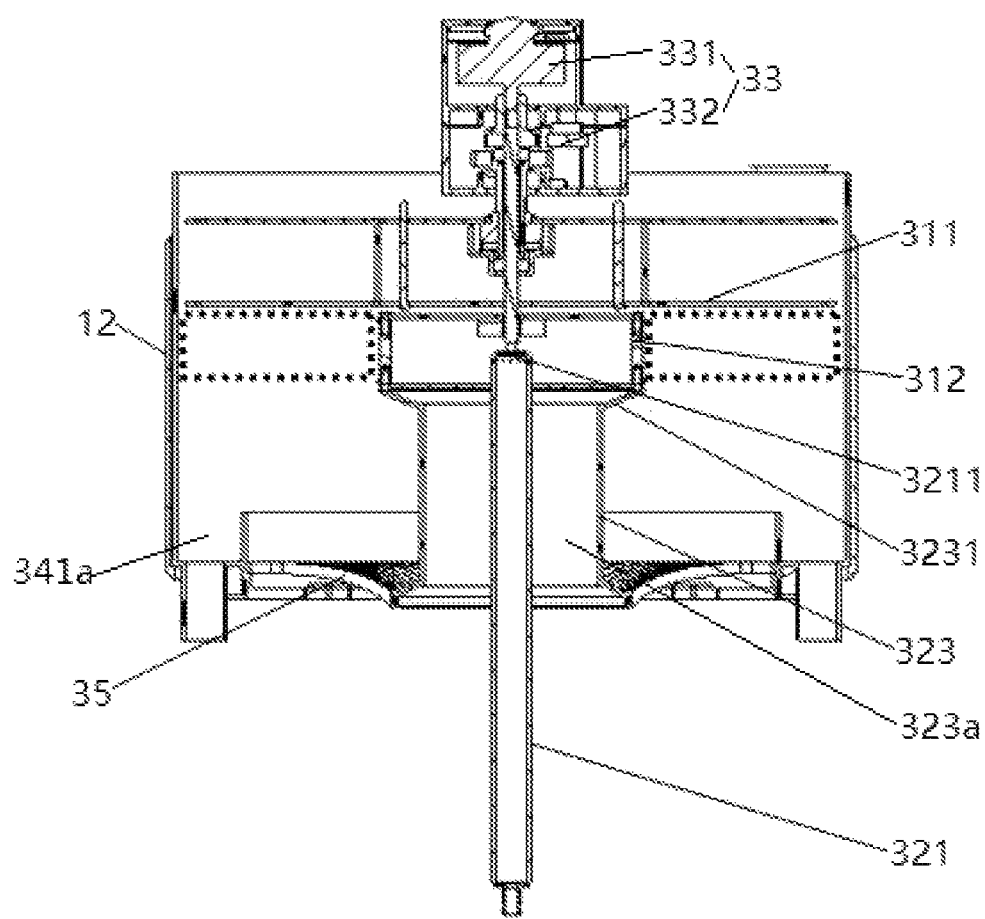
FIG. 10 illustrates a schematic diagram of a purifying member of an air purifier according to an embodiment of the disclosure.

As shown in FIG. 10, further, the purifying member 30 includes a first grille 35. The outer circumference of the first grille 35 is detachably connected with the lower edge of the transparent part, which is convenient to assemble and disassemble the first grille 35, and is convenient to maintain and replace the first grille. The inner circumference of the first grille 35 radially extends towards the water inlet pipe 321. The inner circumference of the first grille 35 is arranged adjacent to the water inlet pipe 321. The first grille 35 includes multiple narrow bars evenly spaced along the circumferential direction, and may comb the airflow passing through it to make the airflow more uniform and stable in the flow process. Meanwhile, the first grille 3 also has a certain decorative effect.

In the description of the disclosure, the meaning of "multiple" is two or more than two.

It is to be noted that in practical applications, the first grille 35 may also be left out to increase ventilation area and reduce pressure loss.

Figure 16:
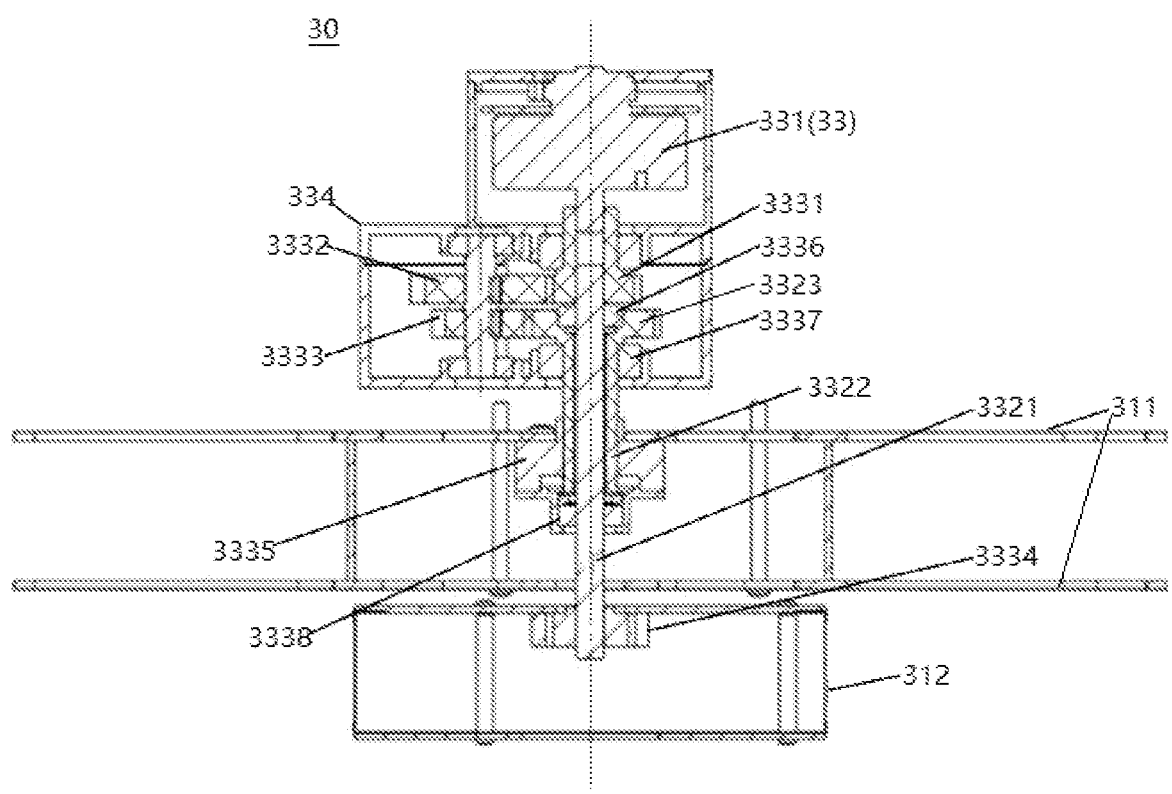
FIG. 16 illustrates a schematic diagram of a purifying assembly and a driving device of an air purifier according to an embodiment of the disclosure.

As shown in FIG. 16, according to yet another embodiment of the disclosure, the driving device 33 includes a motor 331. The motor 331 has a motor 331 shaft. The motor 331 is arranged above the purifying assembly 31 and is connected with the purifying assembly 31. In this way, the purifying assembly 31 is driven by the motor 331 so as to rotate at a high speed in the accommodating cavity 10c, and the motor 331 provides power for the purifying assembly 31 to rotate.

In some examples, the driving device 33 includes a differential assembly 332. The differential assembly 332 is connected with the motor 331, and may control rotation speeds of different rotating members in the purifying assembly 31 to be different from each other; for example, it may control the rotary cylinder and the rotary disk of the purifying assembly 31 to rotate at different rotation speeds. Compared with the manner in the related technology that the rotary cylinder and the rotary disk of the air purifying device are driven together, differential transmission between the rotary cylinder and the rotary disk of the purifying assembly 31 may be realized, so as to achieve better purification performance. Moreover, through the coordination between the differential assembly 332 and the motor 331, different rotation speeds of different rotating members can be realized in the case of only one motor 331 in the whole structure, which saves the production cost compared with the manner in the related technology that two motors 331 respectively control the corresponding rotating members to rotate at different rotation speeds.

Further, the differential assembly 332 includes an inner output shaft 3321 and an outer output shaft 3322. The motor shaft and the inner output shaft 3321 are set to coaxially rotate at the same speed, the outer output shaft 3322 is arranged around the inner output shaft 3321, and at the same time, the outer output shaft 3322 is connected with the inner output shaft 3321 through a driving member. In this way, the inner output shaft 3321 and the outer output shaft 3322 may maintain different rotation speeds, and the rotation speeds of the members respectively driven by the inner output shaft 3321 and the outer output shaft 3322 are different too, which can effectively avoid failure to achieve the optimal performance due to the same rotation speed of the inner output shaft 3321 and the outer output shaft 3322, thus improving the efficiency of the whole machine.

It is to be noted that the driving member between the outer output shaft 3322 and the inner output shaft 3321 may be a friction wheel drive mechanism, a screw drive mechanism, a gear set, a belt driving member, a chain driving member, and so on, namely all members that may realize the differential drive between the outer output shaft 3322 and the inner output shaft 3321, which is not specifically defined in the disclosure.

In some examples, the driving member includes a gear set. The gear set includes a first gear 3331, a second gear 3332 and a third gear 3333. Specifically, the first gear 3331 is arranged around the inner output shaft 3321, and the first gear 3331 is configured to rotate synchronously with the inner output shaft 3321. The second gear 3332 is engaged with the first gear 3331. As shown in FIG. 16, the second gear 3332 is located at the left side of the first gear 3331 and is at the same axial height with the first gear 3331. The first gear 3331 and the inner output shaft 3321 rotate at the same speed; and the first gear 3331 is engaged with the second gear 3332 to drive the second gear 3332 to rotate.

Further, the third gear 3333 and the second gear 3332 are coaxial and rotate synchronously. It is understandable that a vertical shaft runs through the second gear 3332 and the third gear 3333, and the vertical shaft is arranged parallel to the inner output shaft 3321 (as shown in FIG. 16, the vertical shaft is located at the left side of the inner output shaft 3321). The vertical shaft is fixedly connected with the second gear 3332 and the third gear 3333. The second gear 3332 and the third gear 3333 are arranged apart along an extension direction of the vertical shaft. The second gear 3332 drives the vertical shaft to rotate, which in turn drives the third gear 3333 to rotate, so the second gear 3332 and the third gear 3333 rotate coaxially at the same speed.

Moreover, there is a toothed part 3323 arranged on the outer output shaft 3322, and the third gear 3333 is engaged with the toothed part 3323 on the outer output shaft 3322. As shown in FIG. 16, the toothed part 3323 is located directly below the first gear 3331 and is engaged with the third gear 3333, and the third gear 3333 drives the toothed part 3323 to rotate, which in turn drives the outer output shaft 3322 to rotate. To sum up, with the connection between the outer output shaft 3322 and the inner output shaft 3321 through the gear set, the differential drive between the inner output shaft 3321 and the outer output shaft 3322 may be realized under the driving action of a single motor 331, which avoids that the inner output shaft 3321 and the outer output shaft 3322 are always driven at the same speed. When a differential device is applied to the air purifier 100, energy consumption may be saved and the best working performance may be achieved.

In some examples, the inner output shaft 3321 is connected with one of the rotary disk and the rotary cylinder of the purifying assembly 31, and the outer output shaft 3322 is connected to the other of the rotary disk and the rotary cylinder of the purifying assembly 31. Because the rotation speeds of the inner output shaft 3321 and the outer output shaft 3322 of the differential device are different, the rotation speeds of the rotating wheels correspondingly driven by the inner output shaft 3321 and the outer output shaft 3322 are different too. For example, the inner output shaft 3321 is connected with the rotary cylinder of the purifying assembly 31, and the outer output shaft 3322 is connected with the rotary disk of the purifying assembly 31; in this way, the inner output shaft 3321 drives the rotary cylinder to rotate, the outer output shaft 3322 drives the rotary disk to rotate, and the rotation speeds of the rotary cylinder and the rotary disk are different. In the case of the need for a higher rotation speed of the rotary disk, the rotary cylinder may rotate at a lower speed, and in the case of the need for a higher rotation speed of the rotary cylinder, the rotary disk may rotate at a lower speed, which prevents unnecessary energy consumption, achieves the best purification performance, and saves energy consumption; and only one motor 331 is needed for driving, which will not cause cost increase and improves work efficiency.

It is to be noted that the inner output shaft 3321 may also be connected with the rotary disk of the purifying assembly 31, and the outer output shaft 3322 is connected with the rotary cylinder of the purifying assembly 31, which may also improve the purification performance of the purifying assembly 31.

Further, the differential assembly 332 includes a first connecting member 3334 and a second connecting member 3335. For example, the inner output shaft 3321 is fixedly connected with the rotary cylinder through the first connecting member 3334, which may make the rotary cylinder and the inner output shaft 3321 better keep synchronous rotation. The outer output shaft 3322 is fixedly connected with the rotary disk through the second connecting member 3335, which enables the rotary disk and the outer output shaft 3322 to rotate synchronously, that is, the rotary disk and the outer output shaft 3322 keep the same rotation speed.

According to another example of the disclosure, the differential device includes a bearing assembly. The bearing assembly is arranged on the inner output shaft 3321 and the outer output shaft 3322, and is configured to support the inner output shaft 3321 and the outer output shaft 3322 to rotate, so as to reduce the friction coefficient during the movement of the inner output shaft 3321 and the outer output shaft 3322 and improve the rotation accuracy.

According to yet another example of the disclosure, the bearing assembly includes a first bearing 3336 and a second bearing 3337. An accommodating groove is arranged on the side, facing the motor 331, of the toothed part 3323, that is, the accommodating groove is arranged on the top of the toothed part 3323. The first bearing 3336 is arranged around the inner output shaft 3321, and the first bearing 3336 is fitted in the accommodating groove, which can support the rotation of the inner output shaft 3321, reduce the friction coefficient during the rotation of the inner output shaft 3321, and improve the rotation accuracy of the inner output shaft 3321.

Moreover, the differential assembly 332 further includes a tank 334. The gear set is arranged in the tank 334. The inner output shaft 3321 and the outer output shaft 3322 extend downward through the bottom wall of the tank 334. A mounting groove is arranged on the inner bottom wall of the tank 334, the second bearing 3337 is fitted in the mounting groove, and the second bearing 3337 is arranged around the outer output shaft 3322, so as to support the rotation of the outer output shaft 3322, reduce the friction coefficient during the rotation of the outer output shaft 3322, and improve the rotation accuracy of the outer output shaft 3322.

Further, the differential assembly 332 further includes a third bearing 3338. The third bearing 3338 is arranged on the side, away from the motor 331, of the second connecting member 3335. As shown in FIG. 16, the third bearing 3338 is arranged at the bottom end of the second connecting member 3335, and the third bearing 3338 is arranged around the inner output shaft 3321, so as to support the rotation of the inner output shaft 3321, further reduce the friction coefficient during the rotation of the inner output shaft 3321, and improve the rotation accuracy of the inner output shaft 3321.

According to yet another embodiment of the disclosure, the purifying member 30 includes a fan. The fan is arranged above the purifying assembly 31, and is configured to drive the air to flow from the air inlet 10*a* to the air outlet 10*b* through the purifying assembly 31. The driving device 33 like the motor 331 is connected with the fan to drive the fan to rotate, namely providing power for the fan to rotate. Thus, by arranging the fan above the purifying assembly 31, the fan rotates at a high speed under the drive of the motor 331, so as to drive the air to enter the accommodating cavity 10*c* of the housing 10 from the air inlet 10*a* and flow towards the air outlet 10*b*. For example, the fan may drive the air to flow from the air inlet 10*a* to the air outlet 10*b*, which can drive the air to flow and avoid the pressure loss; besides, the fan and the purifying assembly 31 are driven by the same motor 331, so the structure is simple, the foot space is small, and the energy consumption is low.

In some examples, the water supply member 20 includes a water tank 21. The water tank 21 has a water inlet and a water outlet. A water storage cavity 20*a* is defined in the water tank 21. The water storage cavity 20*a* is configured to accommodate water for purifying the air. The water storage cavity 20*a* is in communication with the water inlet and the water outlet. The water in the water storage cavity 20*a* may be discharged through the outlet, and the water can be injected into the water storage cavity 20*a* through the inlet, so as to replace the water in the water storage cavity 20*a* and ensure the purification performance of the air purifier 100.

It is to be noted that the liquid in the water tank 21 is a cleaning liquid of a hyper-gravity member, and in practice it may be various liquids and a mixed liquid.

It is to be noted that the water tank 21 may be integrally formed with the housing 10, that is, the bottom of the accommodating cavity 10c may form the water storage cavity 20a. The water tank 21 may also be a separate tank, that is, the water storage cavity 20a is a separate cavity relative to the accommodating cavity 10c. Specifically, the water tank 21 is movably arranged at the bottom of the accommodating cavity 10c, for example, the water tank 21 may slide relative to the bottom of the accommodating cavity 10c.

Figure 17:
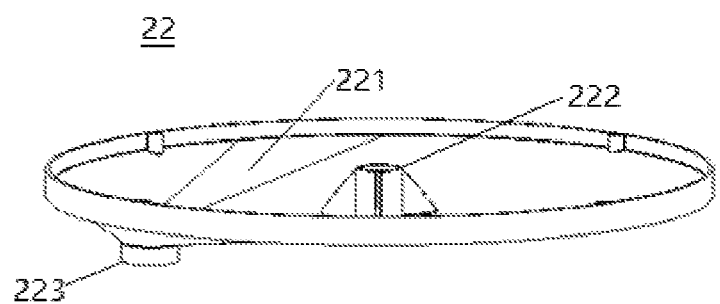
FIG. 17 illustrates a schematic diagram of a water collecting portion of an air purifier according to an embodiment of the disclosure.

Referring to FIG. 4 and FIG. 17, in some examples, the water supply member 20 includes a water collecting part 22. The water collecting part 22 is arranged between the guide member 34 and the water tank 21. The water collecting part 22 is in communication with the guide member 34 and the water tank 21. The water collecting part 22 defines a water collecting groove 221, which may guide the water in the guide member 34 back to the water storage cavity 20a. It is understandable that the water in the water tank 21 is conveyed upward along the water inlet pipe 321 by the water driving member 322, and sprayed into the purifying assembly 31 through the water discharge end 3211 of the water inlet pipe 321. The purifying assembly 31 tears the water and throws it onto the inner wall of the accommodating cavity 10c. The droplets is accumulated on the inner wall of the accommodating cavity 10c to form liquid, and then the liquid flows to the guide member 34 and continues flowing downwards, and enters the water tank 21 through the water collecting part 22.

In an example, the water collecting part 22 is arranged above the water tank 21. The upper end of the water collecting part 22 is directly connected with the surrounding inner wall of the accommodating cavity 10c. The water collecting part 22 is formed in a V-shaped structure, that is, the cross-sectional area of the upper end of the water collecting groove 221 is greater than that of the lower end, and the cross-sectional area of the water collecting groove 221 decreases gradually from top to bottom; in this way, it is convenient to collect the water on the surrounding inner wall of the accommodating cavity 10c, and the water may flow down the inner wall of the water collecting groove 221 into the water tank 21, which achieves an effect of collecting and guiding the water on the inner wall of the accommodating cavity 10c.

As shown in FIG. 17, further, a connecting pipe 25 is connected to the water tank 21, a center interface 222 is arranged at the center of the water collecting part 22, the upper end of the center interface 222 is connected with the water inlet pipe 321, and the lower end of the center interface 222 is connected with the connecting pipe 25, that is, the connecting pipe 25 and the water inlet pipe 321 are connected through the center interface 222. In this way, the water inlet pipe 321 is in communication with the water tank 21 by the connecting pipe 25, and the liquid in the water tank 21 may enter the water inlet pipe 321 through the connecting pipe 25. A water collecting interface 223 is arranged on the lower end of the water collecting part 22. The water flowing down from the inner wall of the guide member 34 or the accommodating cavity 10c may flow along the water collecting part 22 to the water collecting interface 223, and flow back to the water tank 21 through the pipe connected with the water collecting interface 223.

In some examples, the water supply member 20 includes a base 23 and a guide rail 24. The base 23 is supported at the bottom of the water tank 21, and forms the base wall of the accommodating cavity 10c. The guide rail 24 is fixed on the base 23. The water tank 21 is slideably arranged on the guide rail 24. It is understandable that after the water in the water tank 21 is recycled for a period of time, the water in the water tank 21 contains a lot of pollutants, and when the water needs to be replaced, the housing 10 at the corresponding position of the water supply member 20 is removed, and then the water tank 21 may be conveniently removed from the guide rail 24 to replace the water in the water tank 21.

Figure 18:
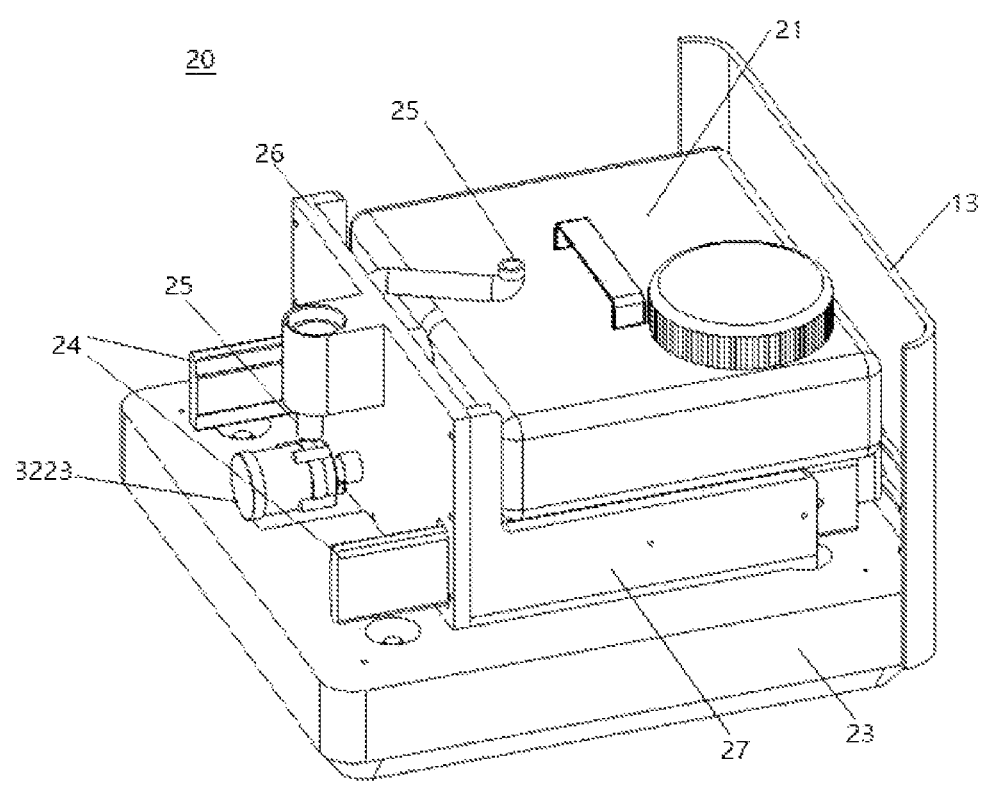
FIG. 18 illustrates a perspective view of a water supply member of an air purifier according to an embodiment of the disclosure.
Figure 19:
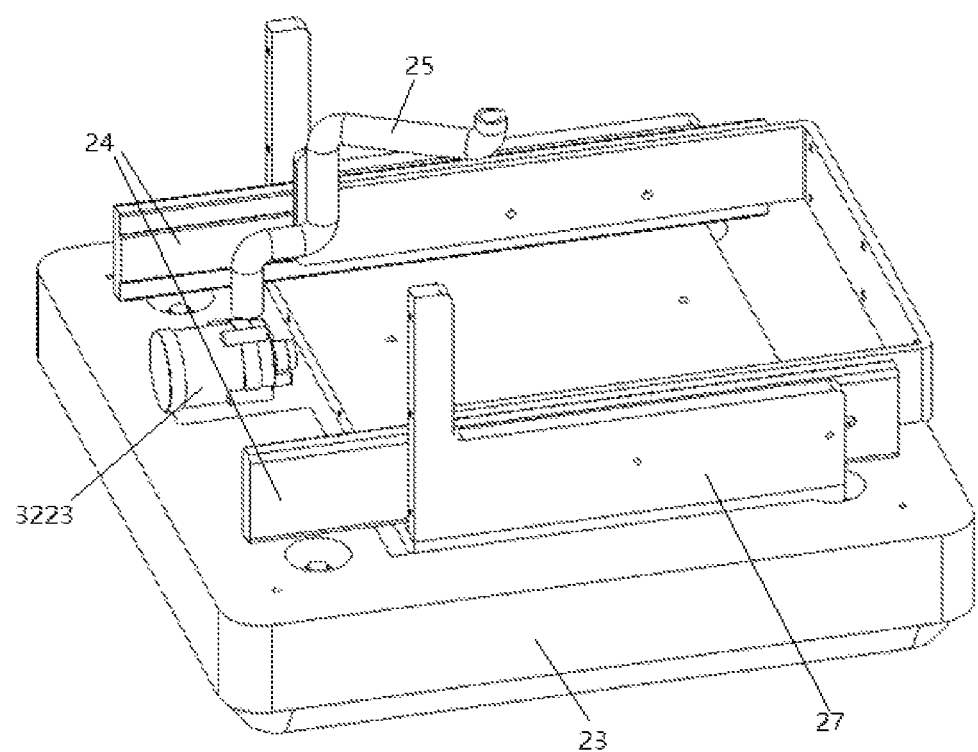
FIG. 19 illustrates a schematic diagram of a base of an air purifier according to an embodiment of the disclosure.

As shown in FIG. 18 and FIG. 19, there are two guide rails 24 arranged on the base 23. The two sides of the water tank 21 are respectively connected with the guide rails 24, that is, the two sides of the water tank 21 may slide on the guide rails 24, the water tank 21 may slide out of the guide rails 24, so as to realize the replacement of the water in the water storage cavity 20a; and after the replacement, the water tank 21 is fitted on the guide rail 24 and then slides back to the base 23.

Further, there are rollers 231 arranged at the bottom of the base 23, for example, there may be three or four rollers 231 at the bottom of the base 23, which is convenient for carrying the air purifier 100. When the air purifier 100 needs to be moved, the air purifier 100 can be directly pushed, which not only saves time and effort, but also makes less noise in the moving process.

Moreover, the water supply member 20 further includes a fixing plate 26, the outer sides of the two guide rails 24 on the base 23 are respectively provided with connecting plates 27, and the fixing plate 26 is connected with the connecting plates 27. Specifically, two ends of the fixing plate 26 are detachably connected with the connecting plates 27, for example, the two ends of the fixing plate 26 are connected with the connecting plates 27 by bolts. The fixing plate 26 has a limiting effect on the water tank 21. When the water tank 21 slides back to the base 23 through the guide rail 24, the fixing plate 26 fixes the water tank 21 at a predetermined mounting position of a sliding rail to prevent the water tank 21 from shaking on the base 23, so as to ensure the stability and reliability of the structure.

In an example, the air purifier 100 further includes an electrolyzing device 50, and the electrolyzing device 50 is arranged in the accommodating cavity 10c to purify the liquid in the accommodating cavity 10c. Specifically, after absorbing formaldehyde, bacteria and other organic compounds in the air, the water is thrown onto the inner wall of the accommodating cavity 10c by the purifying assembly 31. It is understandable that after purifying the air, the water flows back down to the water storage cavity 20a along the inner wall of the accommodating cavity 10c. By arranging in the housing 10 the electrolyzing device 50 which can purify the liquid, after water absorbs formaldehyde and other organic compounds in the air, the formaldehyde and other organic compounds may be removed by electrolysis. In this way, in the process of water recycling, the re-release to the air of the formaldehyde and other organic compounds is avoided, and the efficiency of purifying the formaldehyde and other organic compounds in the air is improved.

Figure 20:
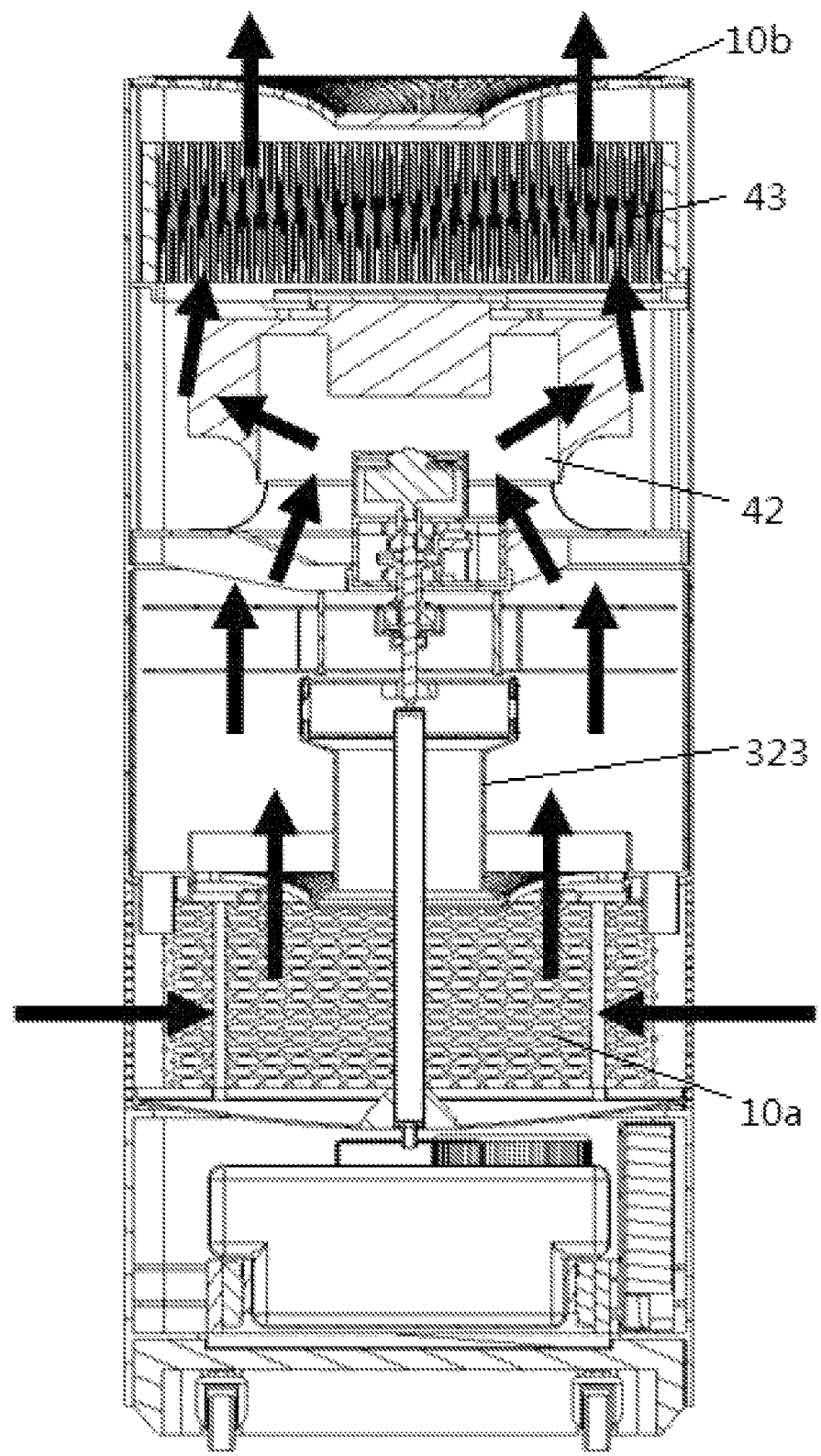
FIG. 20 illustrates a schematic diagram of an air flow path of an air purifier according to an embodiment of the disclosure.

As shown in FIG. 20, according to yet another embodiment of the disclosure, the electrolyzing device 50 is directly arranged in the water storage cavity 20a to purify the liquid in the water storage cavity 20a. It is understandable that after absorbing formaldehyde, bacteria and other organic compounds in the air, the water is thrown onto the inner wall of the accommodating cavity 10c by the purifying assembly 31, and slides down the inner wall of the accommodating cavity 10c to the water storage cavity 20a. The electrolyzing device 50 electrolyzes the formaldehyde and other organic compounds in the water in the water storage cavity 20a, and then the formaldehyde and other organic compounds are degraded into non-toxic and harmless inorganic small molecules; that is, the electrolyzing device 50 directly purifies the water in the water storage cavity 20a continuously, so as to remove the organic pollutants in the water in the water storage cavity 20a, thus improving the efficiency of purifying the air during recycling.

According to yet another embodiment of the disclosure, the electrolyzing device 50 is arranged between the guide member 34 and the water storage cavity 20a and is in communication with each of the guide member and the water storage cavity. The guide member 34 below the purifying assembly 31 may collect in the circumferential direction the water flowing down the inner wall of the accommodating cavity 10c, and the guide member 34 guides the water towards the electrolyzing device 50. In this way, the water after air purification is first guided to the electrolyzing device 50 through the guide member 34 to be purified by the electrolyzing device 50, and then the water is recycled, which effectively prevents the water after air purification from releasing organic molecules such as formaldehyde into the air again, thus improving the air purification efficiency.

According to yet another embodiment of the disclosure, the electrolyzing device 50 includes a water collecting housing and an electrode. The water collecting housing is provided with a water inlet hole and a water outlet hole, and a water collecting cavity is defined in the water collecting housing. The water collecting cavity is in communication with the water inlet hole and the water outlet hole. The water collecting cavity is in communication with the guide member 34 through the water inlet hole, and is in communication with the water storage cavity 20a through the water outlet hole. The electrode is arranged in the water collecting cavity. The water collecting housing 71 may be polygonal structure, circular structure, elliptic structure, etc.

Specifically, the water in the guide member 34 enters the water collecting cavity through the water inlet hole, and the organic molecules such as formaldehyde and bacteria in the water are degraded through the electrode to become non-toxic and harmless inorganic molecules, thus realizing the effect of purifying the water. The purified water is discharged into the water storage cavity 20a through the water outlet hole to recycle the water and save water resources, besides, the organic molecules such as formaldehyde may be effectively removed from the water, and the efficiency of purifying the air may be improved.

According to yet another embodiment of the disclosure, the air moving member 40 includes a support frame 41, a blower 42 and a filtering member 43. The support frame 41 is arranged on the inner wall of the accommodating cavity 10c. The upper end of the purifying member 30 is fixed at the lower side of the support frame 41. The blower 42 is fixed on the support frame 41 to pump airflow from the air inlet 10a to the air outlet 10b, and provides power for the airflow. The support frame 41 is configured to fix the blower 42 and the purifying member 30. The filtering member 43 is arranged above the blower 42 to further filter and purify the airflow, which ensures that the airflow discharged through the air outlet 10b is clean. In an example, the filtering member 43 may also be arranged below the blower 42. The filtering member 43 may be a filtering sieve, and the filtering sieve may be fixed through a bracket 45.

Specifically, the blower 42 provides power for the airflow to flow. The airflow enters the accommodating cavity 10c from the air inlet 10a and moves upwards. After flowing through the purifying member 30, the airflow flows through the blower 42, and continues flowing through the filtering member 43 above, then, the remaining particulate pollutants and gas pollutants in the airflow are removed by the filtering member 43 and finally discharged from the air outlet 10b.

It is understandable that compared with the purifying device in the related technology, the air purifier 100 in the embodiments of the disclosure purifies the air by washing at first, and then further purifies the air purified by washing through the filtering member 43 like the filtering sieve, for example, filters the remaining particles in the air; here, purifying by washing refers to a purification mode of gas-liquid separation after capturing and absorbing pollutants in the air by water in the air purifier 100 of the embodiments of the disclosure. In this way, not only the purity of air purification is ensured, but also the frequency of replacing the filtering member 43 regularly is reduced; even it is not necessary to replace the filter sieve, but to replace the water regularly, so it is easy to use, the cost for later replacement and maintenance is reduced, and the user experience is good.

In some examples, the blower 42 is a multi-vane centrifugal blower 42. By using the multi-vane centrifugal blower 42, the air flow direction in the air purifier 100 may be shown in FIG. 20, that is, the airflow flows from air inlet 10a to the accommodating cavity 10c and flows upward. After the airflow flows through the purifying assembly 31 and passes through the area where the blower 42 is, a flow state of the airflow is formed as that it first narrows to the central axis, then diffuses around, and flows upward from the edge of the accommodating cavity 10c. The airflow may be accelerated first and then decelerated, and its flow direction is changed, so that a kinetic energy of the airflow is converted into a potential energy (pressure) to increase the pressure of the airflow and discharge the airflow.

In practical applications, an axial flow blower 42, a diagonal blower 42, etc. may also be used. The flow direction of the airflow when flowing through the blower 42 will also be adjusted, which will not be repeated here.

In some examples, the air moving member 40 includes a second grille 44. The second grille 44 is arranged at the air outlet 10b. The second grille 44 includes narrow bars evenly spaced along the circumferential direction, and may comb the airflow at the air outlet 10b to make the airflow more uniform and stable when discharged. Besides, the second grille 44 has a decorative effect to make a good appearance experience.

Figure 22:
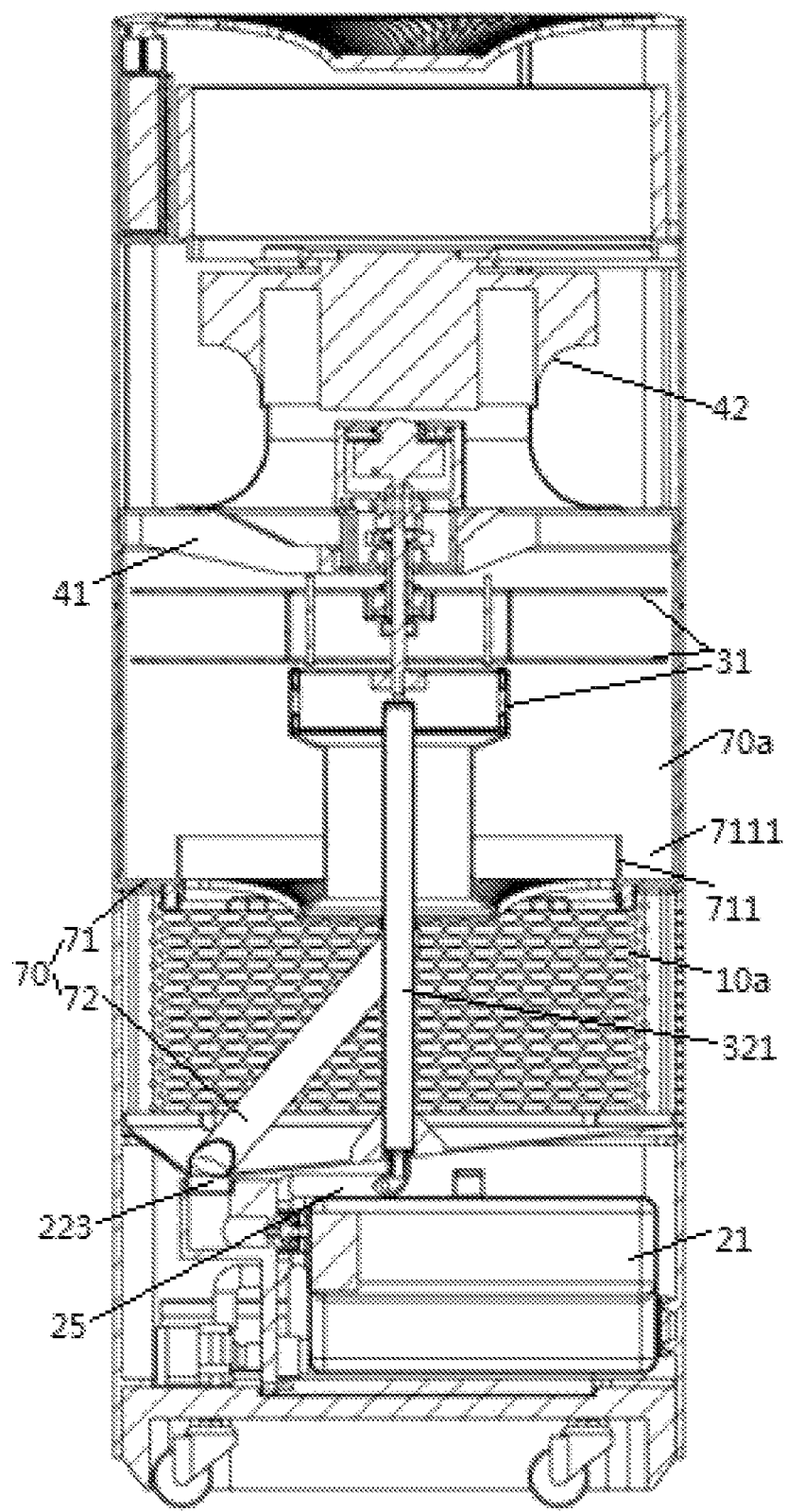
FIG. 22 illustrates a schematic diagram of an air purifier according to another embodiment of the disclosure.
Figure 23:
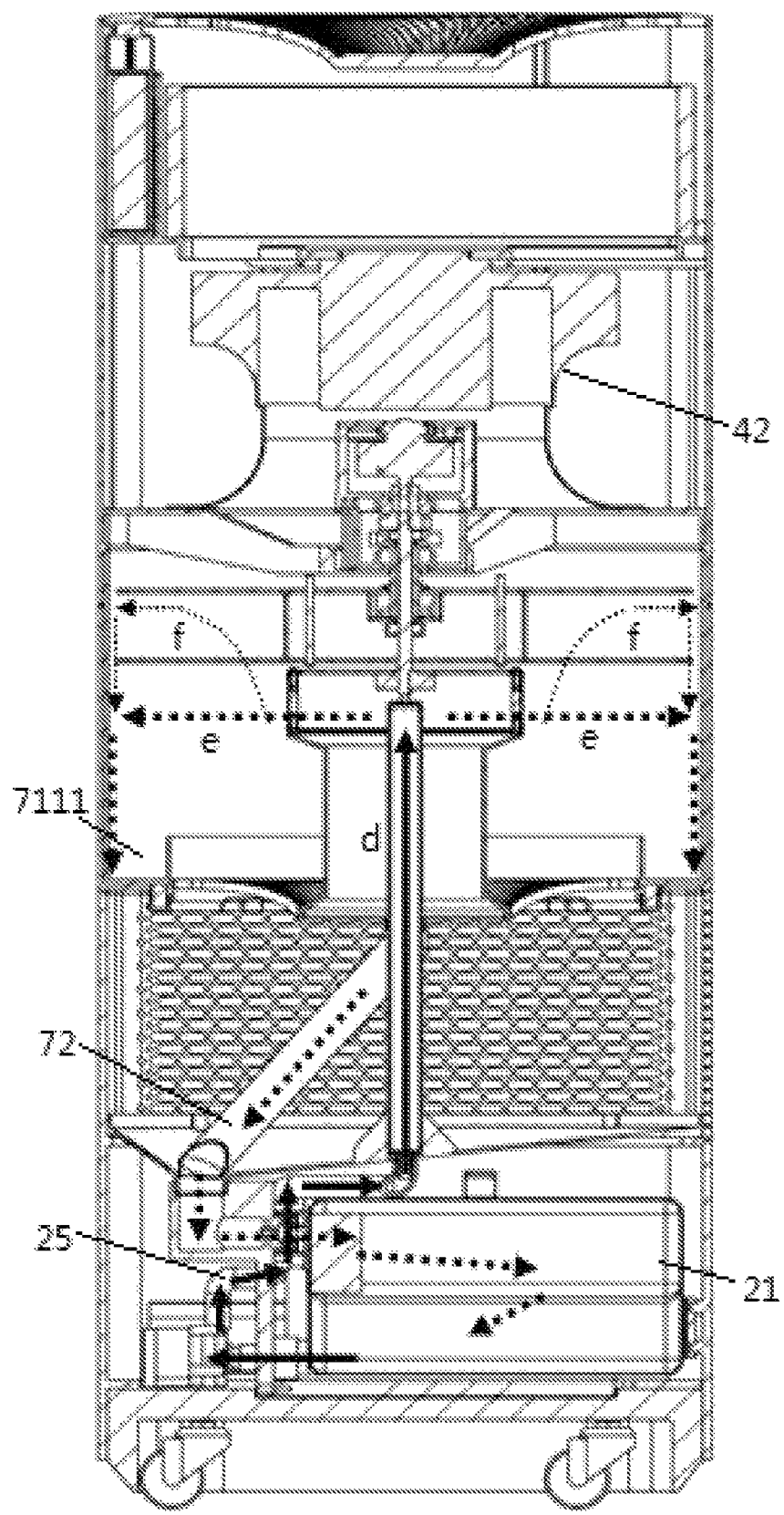
FIG. 23 illustrates a schematic diagram of a liquid flow path of an air purifier according to another embodiment of the disclosure.
Figure 24:
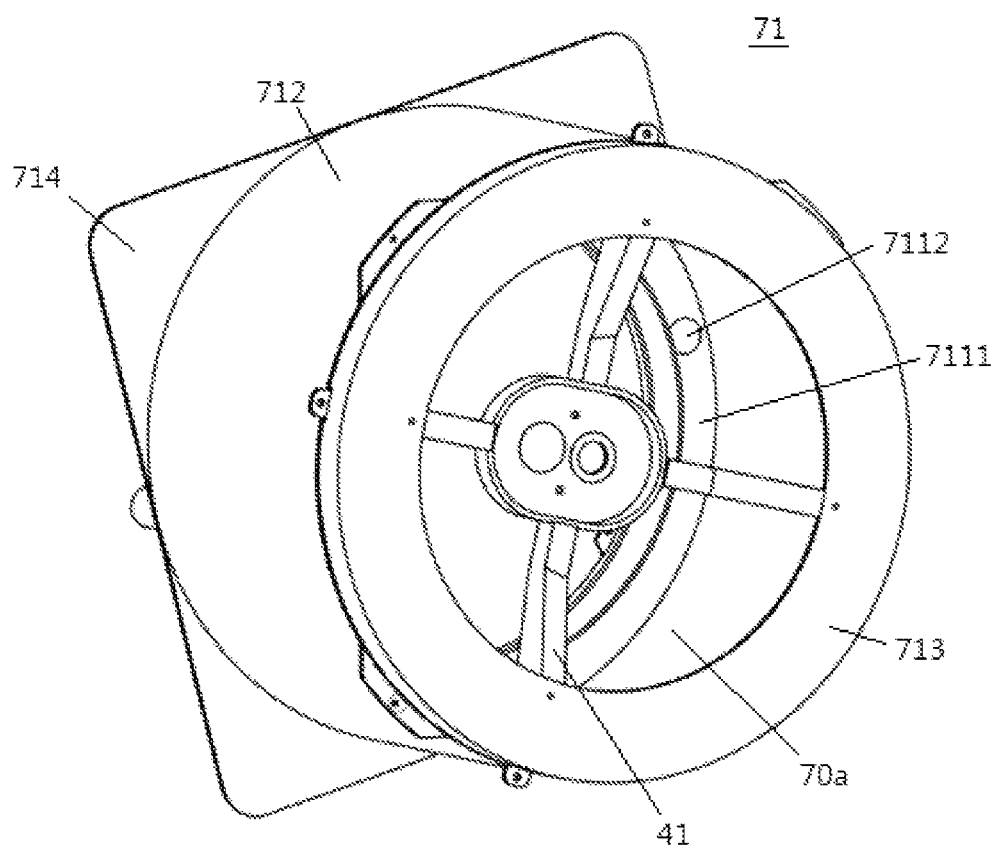
FIG. 24 illustrates a perspective view of an accommodating member of an air purifier according to yet another embodiment of the disclosure.

As shown in FIG. 22 to FIG. 24, according to yet another example of the disclosure, the air purifier 100 further includes a watertight structure 70, which is fixedly connected with the inner wall of the accommodating cavity 10c. Specifically, the watertight structure 70 may be fixed on the inner wall of the accommodating cavity 10c through the connecting member. The watertight structure 70 is in communication with the water storage cavity 20a. An accommodating space 70a is defined in the watertight structure 70 and is configured to accommodate the liquid flowing out of the air purifier 100 after being poured.

Specifically, when the air purifier 100 is dumped, and even when the air purifier 100 is dumped to lie flat on the ground, the water in water storage cavity 20a flows out. By arranging a watertight structure 70 in communication with the water storage cavity 20a, the water in the water storage cavity 20a flows into the accommodating space 70a, that is, the accommodating space 70a can accommodate the water leaking out of the water storage cavity 20a, so as to prevent the water from flowing out of the housing 10 from the air inlet 10a or the air outlet 10b.

Further, the volume of the accommodating space 70a is larger than that of the water storage cavity 20a. Here, the accommodating space 70a refers to the size of the space that can accommodate the water capacity without leakage. When the air purifier 100 is dumped, for example, the air purifier 100 lies flat on the ground, even if all the water in the water storage cavity 20a leaks out, the water may be accommodated in the accommodating space 70a, which ensures that when all the water leaks out of the water storage cavity 20a, the water can still be accommodated in the accommodating space without overflow.

As shown in FIG. 22, in some examples, the watertight structure 70 includes an accommodating member 71 and a directing member 72. The accommodating member 71 defines the accommodating space 70a. The purifying assembly 31 is located in an axial area surrounded by the accommodating space 70a. A flow collecting part 711 is arranged on the accommodating member 71, and the flow collecting part 711 is located above the air inlet 10a. A flow collecting groove 7111 is defined in the flow collecting part 711, and the flow collecting groove 7111 is provided with a drainage mouth 7112. A flow guide channel is defined in the directing member 72, one end of the flow guide channel is connected with the drainage mouth 7112, and another end of the flow guide channel is connected with the water storage cavity 20a. It is understandable that when the air purifier 100 runs, the water in the flow collecting groove 7111 may enter the water storage cavity 20a through the drainage channel; when the air purifier 100 is dumped, the water in the water storage cavity 20a may flow into the accommodating space 70a through the drainage channel, which may effectively prevent the water from splashing out or flowing out of the air inlet 10a.

The water collecting part 711 of the embodiments of the disclosure has dual functions. One function is that when the air purifier 100 operates, the water distribution assembly 32 guides the water in the water storage cavity 20a upwards and distributes water into the purifying assembly 31, the purifying assembly 31 throws the water after purifying the airflow and the captured droplets onto the inner wall of the accommodating space 70a, and the water slides down the inner wall of the accommodating space 70a into the flow collecting groove 7111, at this point, the flow collecting part 711 has the function of accepting and collecting the water on the inner wall of the accommodating space 70a, which may prevent the water from splashing out from the air inlet 10a in the process of flowing down. The other function is that the accommodating space 70a is defined between the flow collecting part 711 and the inner wall of the accommodating space 70a, and when the air purifier 100 is dumped, the accommodating space 70a may accommodate the water leaking from the water storage cavity 20a and the water discharge end of the water distribution assembly 32, so as to prevent the water from leaking out of the housing 10 from the air inlet 10a.

Further, the accommodating member includes a cylindrical body, an upper retainer ring and a lower retainer ring. The cylindrical body is connected with the inner wall of the accommodating cavity 10c. The section of the cylindrical body may be consistent with the section of the housing 10, for example, they are all round. The section of the cylindrical body may also be inconsistent with the section of the housing 10, for example, the section of the cylindrical body is round and the section of the housing 10 is square; in this case, the housing 10 and the cylindrical body may be connected through the inner wall of the accommodating cavity 10c or a connection portion 714 on the outer wall of the cylindrical body 712.

The upper retainer ring 713 is arranged on the upper end of the cylindrical body. The upper retainer ring 713 may shield the gap between the outer circumference of the blower 42 and the inner wall of the accommodating cavity 10c. After water flows into the accommodating space 70a, the upper end of the cylindrical body 712 may be closed through the upper retainer ring 713, which effectively prevents water from flowing out of the gap between the outer circumference of the blower 42 and the inner wall of the accommodating cavity 10c. The support frame 41 is fixedly connected on the inner circumference of the upper retainer ring 713. The lower retainer ring is arranged on the lower end of the cylindrical body 712, and the lower retainer ring and the cylindrical body 712 may be formed integrally. The lower retainer ring forms the flow collecting part 711. An annular accommodating space 70a is defined among the inner wall of the cylindrical body 712, the flow collecting part 711 and the upper retainer ring 713, the space configured to accommodate the leaking water during the dumping is constructed by the three in combination. The capacity of the water storage cavity 20a does not exceed the capacity of the annular accommodating space 70a, so as to ensure that the water in the water storage cavity 20a can be accommodated within the annular accommodating space 70a even if all the water in the water storage cavity 20a leaks out.

In an example, the lower end of the directing member 72 may be connected with the water collecting interface 223 of the water collecting part 22, and the upper end of the directing member 72 is connected with the flow collecting part 711. In this way, the water in the flow collecting groove 7111 may flow down along the drainage channel, passes through the water collecting interface 223 and back to the water storage cavity 20a. When the air purifier 100 is dumped, the water in the water storage cavity 20a may also flow to the accommodating space 70a in an opposite direction.

In an example, the water tank 21 defines the water storage cavity 20a. Because the water tank 21 is mounted on the guide rail 24 with a self-locking function, the water tank 21 is reliably connected with the water collecting part 22. One end of the drainage channel is in communication with the flow collecting groove 7111 and another end is in communication with the water collecting part 22, and the flow collecting part 711 and the water collecting part 22 are respectively fixed on the inner wall of the accommodating cavity 10c by screws, so as to ensure the reliable connection of the directing member 72, the flow collecting part 711 and the water collecting part 22. One end of the connecting pipe 25 is tightly connected with the water pump 3223 and another end is tightly connected with the water inlet pipe 321, the water pump 3223 is fixed on the inner wall of the accommodating cavity 10c by screws, and the water inlet pipe 321 is tightly connected with the water collecting part 22. In this way, the water pump 3223, the connecting pipe 25 and the water inlet pipe 321 are reliably connected, namely the whole waterway system. After the air purifier 100 is dumped, the water in the water storage cavity 20c only flows out from the drainage mouth 7112 of the flow collecting part 711 and the water discharge end 3211 on the water inlet pipe 321.

Specifically, if when the air purifier 100 tilts, a water level is lower than the drainage mouth 7112 of the flow collecting part 711 and the water spray nozzle on the water discharge end 3211 of the water inlet pipe 321, the water will not flow out; if after the air purifier 100 is dumped, the water level is higher than the drainage mouth 7112 of the flow collecting part 711 and the water spray nozzle on the water discharge end 3211 of the water inlet pipe 321, the water will flow and flow into the accommodating space 70*a* of the watertight structure 70, which may prevent the water from flowing out of the housing 10, that is, prevent the water from flowing out of the housing 10 after the air purifier 100 is dumped.

As shown in FIG. 23, when the air purifier 100 runs, the water in the water tank 21 flows upward along the water inlet pipe 321 under the drive of the water pump 3223 (the direction of arrow as shown in d in FIG. 23), and is sprayed into the rotary cylinder through the water discharge end 3211 of the water inlet pipe 321. Under the action of centrifugal force generated when the rotary cylinder rotates at a high speed, the water coming out of the water spray nozzle is torn and further refined into droplets that may meet the rising air and catch pollutants in the airflow, and is thrown onto the inner wall of the accommodating space 70*a* (the direction of arrow as shown in e in FIG. 23). The airflow continues to rise carrying portion of the droplets, and the rotary disk captures the droplets in the airflow while rotating at a high speed, and throws them onto the inner wall of the accommodating space 70*a* (the direction of arrow as shown in fin FIG. 23). The water accumulates on the inner wall of the accommodating space 70*a* and slides down to the flow collecting groove 7111, and then the water in the flow collecting groove 7111 flows down the inclined drainage channel through the drainage mouth 7112 and enters the water tank 21 through the water collecting interface 223.

Figure 2:
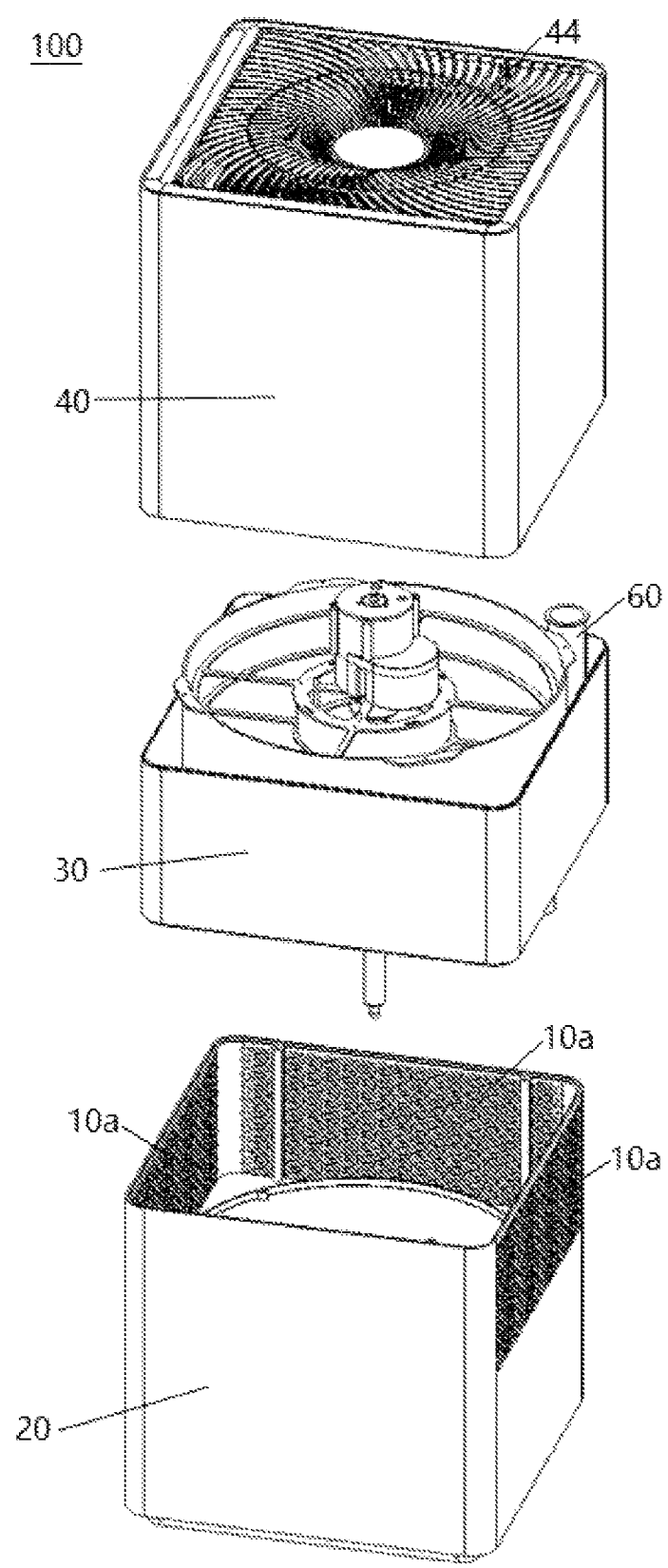
FIG. 2 illustrates an exploded view of an air purifier according to an embodiment of the disclosure.
Figure 3:
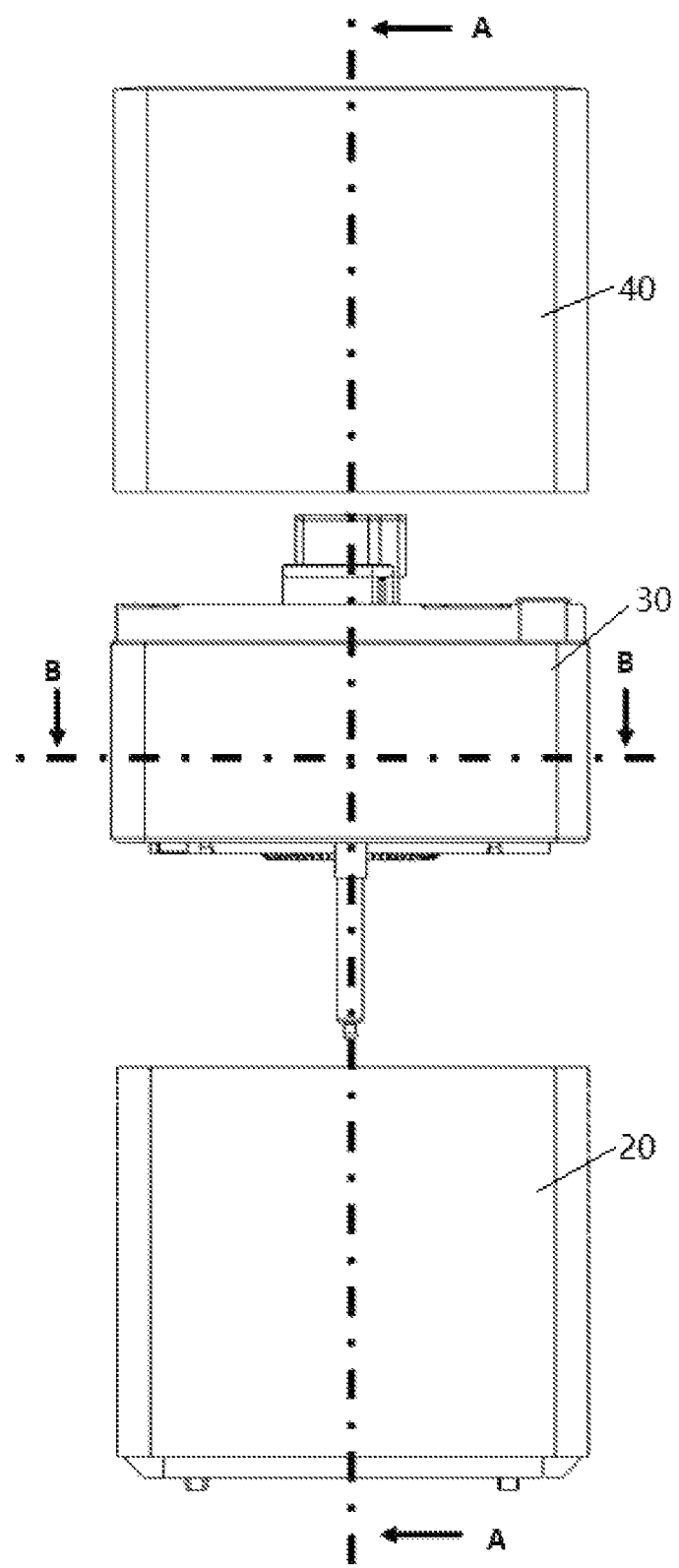
FIG. 3 illustrates a front view of FIG. 2.

According to yet another embodiment of the disclosure, a wire access pipe 60 extending in an axial direction is arranged in the accommodating cavity 10*c*. As shown in FIG. 2, the wire access pipe 60 enables the wires in the water supply member 20 at the lower side to be concentrated on the upper side and gathered with the wires in the air moving member 40, so that the structure appearance is aesthetical and it is easy to control. In practice, the wires in the air moving member 40 at the upper side may also be collected centrally to the lower side. The wires in the water supply member 20 and the air moving member 40 may also be separately collected and managed without arranging the wire access pipe 60.

As shown in FIG. 2 and FIG. 4, according to yet another embodiment of the disclosure, the housing 10 includes a first housing 11, a second housing 12 and a third housing 13 which are detachably connected. The first housing 11 is located above the third housing 13. The second housing 12 is connected between the first housing 11 and the second housing 12. The first housing 11, the second housing 12 and the third housing 13 are successively connected to one another in the vertical direction. The air moving member 40 is located in the first housing 11. The purifying member 30 is located in the second housing 12. The water supply member 20 is located in the third housing 13.

As shown in FIG. 2 and FIG. 4, further, the air inlet 10*a* is arranged on the side wall of the third housing 13, and the edge of the air inlet 10*a* forms a chamfer extending along an air inflow direction; in this way, when entering the accommodating cavity 10*c* from the air inlet 10*a*, the airflow may flow in along the extension direction of the chamfer, so that the airflow may enter the accommodating cavity 10*c* smoothly. The chamfer of the air inlet 10*a* has a drainage effect on the airflow.

As shown in FIG. 2, the air inlet 10*a* may be arranged on three side walls of the third housing 13, and of course, the air inlet 10*a* may also be arranged on four side walls of the third housing 13. The air inlet 10*a* may be square, round, triangle and other shapes, as well as a grille-shaped bar opening, which can be selected according to actual needs, and the disclosure does not make specific restrictions on this.

Figure 21:
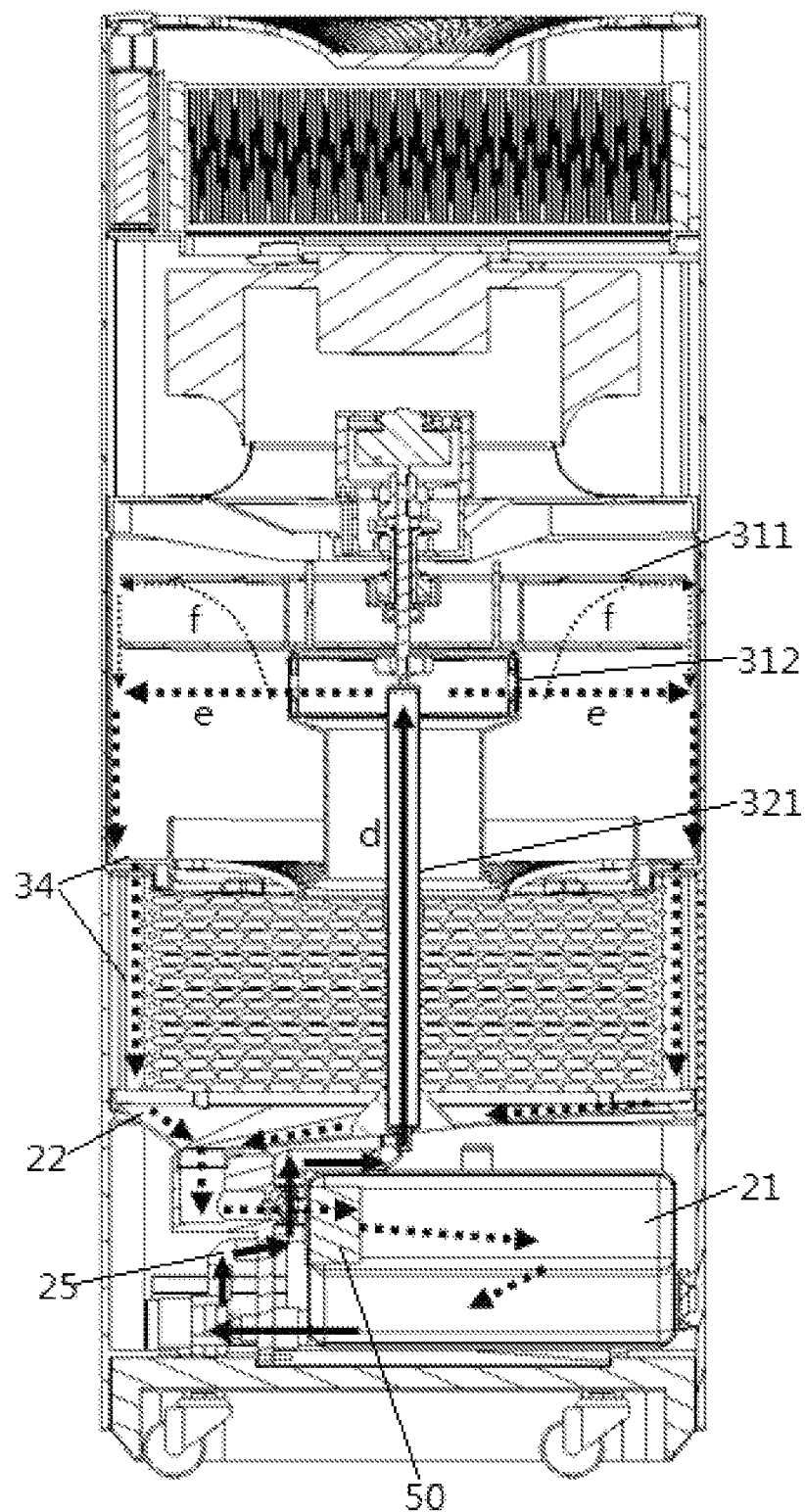
FIG. 21 illustrates a schematic diagram of a liquid flow path of an air purifier according to an embodiment of the disclosure.

The working principle and process of the air purifier 100 in the embodiments of the disclosure are described in detail below according to FIG. 20 and FIG. 21. FIG. 20 illustrates a schematic diagram of an air flow path in the air purifier 100. FIG. 21 illustrates a schematic diagram of a liquid flow path in the air purifier 100.

Referring to FIG. 20 and FIG. 21, when the air purifier 100 runs, the air moving member 40 provides power for the airflow to flow, the airflow enters the accommodating cavity 10*c* from the air inlet on the third housing 13, the air moving member 40 drives the airflow to flow upwards, and at the same time, the water in the water storage cavity 20*a* flows upward through connection the connecting pipe 25 and the water inlet pipe 321 under the drive of water driving member 322 (the direction of arrow as shown in d in FIG. 21). The water is sprayed into the rotary cylinder of the purifying assembly 31 at the water discharge end 3211 of the water inlet pipe 321, and due to the action of centrifugal force generated by the rotary cylinder rotating at a high speed, the sprayed water is torn and dispersed into liquid silk, liquid membrane and other forms. The liquid silk and the liquid membrane are further torn and dispersed into tiny droplets while being thrown through the first mesh of the rotary cylinder (the direction of arrow as shown in e in FIG. 21). The tiny droplets dispersed in the first interval space 315 meet the rising airflow and then may capture the gas, liquid and solid pollutants in the airflow, so the tiny droplets have the effect of purifying the airflow.

The purified airflow continues to flow upward carrying the droplets (the direction of arrow as shown in fin FIG. 21), and the rotary cylinder rotating at a high speed captures the droplet in the airflow and throws it onto the inner wall of the accommodating cavity 10*c*, thus achieving the gas-liquid separation effect. The airflow may flow upward through the second mesh on the rotary disk, and then through the blower 42; and when the airflow continues to flow upward through the filtering member 43, the filtering member 43 further filters the particles in the airflow, so as to further improve the cleanliness and cleanliness of the airflow; finally, the airflow is discharged through the air outlet 10*b*.

The water thrown onto the inner wall of the accommodating cavity 10*c* by the rotary cylinder and the rotary disk accumulates and flows down. The water flows into the water guide groove 341*a* along the inner wall of the accommodating cavity 10*c*, and flows into the water collecting groove 221 along the flow guide channel, and finally flows back to the water storage cavity 20*a* The electrolyzing device 50 in the water storage cavity 20*a* conducts electrolysis on the water to ensure that the water in the water storage cavity 20*a* always keeps in a pure state to ensure the cycle of purification.

In the descriptions of the disclosure, it is to be understood that orientation or position relationships indicated by terms "center", "longitudinal", "transverse", "length", "width", "thickness", "upper", "lower", "vertical", "horizontal", "top", "bottom", "inner", "outer", "clockwise", "counter-clockwise", "axial direction", "radial direction", "circumferential direction" and the like are orientation or position relationships shown in the drawings, are adopted not to indicate or imply that indicated devices or components must be in specific orientations or structured and operated in specific orientations but only to conveniently describe the disclosure and simplify descriptions.

Other components and operations of the air purifier 100 according to the embodiments of the disclosure are known to those of ordinary skill in the art, and will not be described in detail here.

In the descriptions of the specification, the descriptions made with reference to terms "an embodiment", "some embodiments", "exemplary embodiment" "example", "specific example", "some examples" or the like refer to that specific features, structures, materials or characteristics described in combination with the embodiment or the example are included in at least one embodiment or example of the disclosure. In the specification, a schematic representation of the above terms does not necessarily refer to the same embodiment or example. Moreover, the specific described features, structures, materials or characteristics may be combined in a proper manner in any one or more embodiments or examples.

Although the embodiments of the disclosure have been shown and described, those of ordinary skill in the art may understand that: these embodiments may be subject to a variety of changes, modifications, replacements and variants without departing from the principles and purposes of the disclosure, and the scope of the disclosure is limited by the claims and their equivalents.

What is claimed is:

1. An air purifier, comprising:
    a housing provided with an air inlet and an air outlet and defining an accommodating cavity communicating the air inlet with the air outlet, the air inlet being located on a side wall of the housing;
    a water supply member arranged in the accommodating cavity, a water storage cavity being defined in the water supply member;
    a purifying member, the purifying member being arranged in the accommodating cavity and located above the water supply member to purify air, the purifying member comprising:
        a purifying assembly rotatably arranged in the accommodating cavity,
        a water distribution assembly for guiding water in the water supply member to flow upwards and distributing water towards the purifying assembly, wherein the water distribution assembly comprises a water inlet pipe, a water discharge end of the water inlet pipe is provided with a plurality of water injection nozzles, or the water discharge end of the water inlet pipe is in a form of an atomizing nozzle, and the water discharge end of the water inlet pipe is located below the purifying assembly and is spaced apart from the purifying assembly in a vertical direction, and
        a driving device located above the purifying assembly and connected with the purifying assembly to drive the purifying assembly into rotation; and
    an air moving member arranged in the accommodating cavity and located above the purifying member.

2. The air purifier of claim 1, wherein the purifying assembly comprises: a rotary capturing member and a rotary purifying member; the rotary capturing member and the rotary purifying member are configured to rotate in the accommodating cavity; the rotary purifying member is spaced apart from the side wall of the housing; and the rotary capturing member is located above the rotary purifying member.

3. The air purifier of claim 2, wherein the purifying assembly comprises multiple stages; each stage of the purifying assembly comprises the rotary capturing member and the rotary purifying member; and the multiple stages of the purifying assembly are successively connected to one another in an airflow direction.

4. The air purifier of claim 2, wherein the rotary capturing member is in the form of a rotary disk, and the rotary purifying member is in the form of a rotary cylinder; a side wall of the rotary cylinder is provided with a first mesh, and at least a portion of the rotary disk, located between the rotary cylinder and the housing in a radial direction, is provided with a second mesh.

5. The air purifier of claim 4, wherein the purifying assembly comprises a rotary disk and a cylinder; the rotary disk comprise a first rotary disk and a second rotary disk; the first rotary disk and the second rotary disk are rotatable in opposite directions with respect to one another; the first rotary disk is provided with a third mesh; the second rotary disk is provided with a fourth mesh; the second rotary disk is arranged above the first rotary disk and is spaced apart from the first rotary disk in an axial direction; the cylinder is arranged between the first rotary disk and the second rotary disk, and an outer circumferential wall of the cylinder is a cylindrical surface and is spaced apart from the side wall of the housing.

6. The air purifier of claim 4, wherein the driving device comprises a motor having a motor shaft; the motor is arranged above the purifying assembly and is connected with the purifying assembly to drive the purifying assembly into rotation.

7. The air purifier of claim 6, wherein the driving device comprises:
    a differential assembly connected with the motor and configured to control rotation speeds of different rotating members in the purifying assembly to be different.

8. The air purifier of claim 7, wherein the differential assembly comprises:
    an inner output shaft connected with the motor shaft of the motor and configured to rotate around a same axis and at a same speed as the motor shaft; and
    an outer output shaft having a center hole and arranged around the inner output shaft; the outer output shaft is connected with the inner output shaft through a driving member to make a rotation speed of the inner output shaft different from that of the outer output shaft.

9. The air purifier of claim 8, wherein the driving member comprises a gear set; the gear set comprises:
    a first gear arranged around the inner output shaft and configured to rotate synchronously with the inner output shaft;
    a second gear engaged with the first gear; and
    a third gear, the third gear is coaxial with the second gear and is configured to rotate synchronously with the second gear; the outer output shaft is provided with a toothed part, and the third gear is engaged with the toothed part on the outer output shaft.

10. The air purifier of claim 8, wherein the inner output shaft is connected with one of the rotary disk and the rotary cylinder of the purifying assembly, and the outer output shaft is connected with the other of the rotary disk and the rotary cylinder of the purifying assembly.

11. The air purifier of claim 1, wherein the water distribution assembly is arranged below the purifying assembly; the water distribution assembly comprises:

a water driving member, the water driving member is connected with the water inlet pipe to drive water in the water storage cavity to flow upwards.

12. The air purifier of claim 11, wherein the water discharge end of the water inlet pipe extends into the purifying assembly.

13. The air purifier of claim 11, wherein the water driving member comprises:
a water conveying member, the water conveying member is movably arranged in the water inlet pipe to convey liquid upwards; and
a connector, the water conveying member is connected with the purifying assembly through the connector.

14. The air purifier of claim 13, wherein the water conveying member is a screw; the screw is configured to rotate synchronously with the purifying assembly in the water inlet pipe; a conveying space is defined between the screw and an inner wall of the water inlet pipe; and the screw presses the water in the water storage cavity into the conveying space to convey the water upwards.

15. The air purifier of claim 13, wherein the water driving member is a water pump, and the water pump is connected with a water inflow end of the water inlet pipe.

16. The air purifier of claim 11, wherein the water distribution assembly comprises: a partition tube; the partition tube is located below the purifying assembly; the partition tube is arranged around the water inlet pipe, and is coaxial with the water inlet pipe and spaced apart from the water inlet pipe; a lee area is defined between the water inlet pipe and the partition tube.

17. The air purifier of claim 11, wherein a portion of the side wall of the housing radially facing the purifying member is formed as a transparent part.

18. The air purifier of claim 17, wherein the purifying member comprises a first grille; an outer circumference of the first grille is connected with a lower edge of the transparent part, and an inner circumference of the first grille extends radially towards the water inlet pipe.

19. The air purifier of claim 1, wherein the purifying member comprises a guide member; the guide member is arranged below the purifying assembly along a circumferential direction of the housing; and the guide member collects liquid splashed on an inner wall of the accommodating cavity by the purifying assembly and guides the liquid towards the water supply member.

20. The air purifier of claim 19, wherein the guide member comprises an annular water guide part and a flow guider;
the air inlet is located below the purifying assembly; the annular water guide part is arranged between the purifying assembly and the air inlet; the annular water guide part and the inner wall of the accommodating cavity define a water guide groove; the water guide groove is provided with a water guide mouth;
the flow guider axially extends along the inner wall of the accommodating cavity; the flow guider is arranged on the inner wall of the accommodating cavity and defines a flow guide channel together with the inner wall of the accommodating cavity; the flow guide channel is in communication with the water guide mouth.

21. The air purifier of claim 20, wherein the annular water guide part comprises:
an annular base plate forming a bottom wall of the water guide groove; and
an annular baffle connected with the annular base plate in the circumferential direction and spaced apart from the inner wall of the accommodating cavity in a radial direction; the inner wall of the accommodating cavity, the annular base plate and the annular baffle jointly define the water guide groove.

22. The air purifier of claim 19, wherein the water supply member comprises a water tank; the water tank has a water inlet and a water outlet, and the water storage cavity communicating the water inlet with the water outlet is defined in the water tank.

23. The air purifier of claim 22, wherein the water supply member comprises a water collecting part which is arranged between the guide member and the water tank, and is connected with the guide member and the water tank.

24. The air purifier of claim 22, wherein the water supply member comprises:
a base, which is supported at a bottom of the water tank, and forms a bottom wall of the accommodating cavity; and
a guide rail, which is fixed on the base; the water tank is slideably arranged on the guide rail.

25. The air purifier of claim 24, wherein a bottom of the base is provided with a roller.

26. The air purifier of claim 19, further comprising an electrolyzing device, which is arranged in the accommodating cavity to purify the liquid in the accommodating cavity.

27. The air purifier of claim 26, wherein the electrolyzing device is arranged in the water storage cavity to purify the liquid in the water storage cavity.

28. The air purifier of claim 26, wherein the electrolyzing device is arranged between the guide member and the water storage cavity, and is in communication with each of the guide member and the water storage cavity.

29. The air purifier of claim 26, wherein the electrolyzing device comprises a water collecting shell and an electrode;
the water collecting shell is provided with a water inlet hole and a water outlet hole; a water collecting cavity communicating the water inlet hole with the water outlet hole is defined in the water collecting shell; the water collecting cavity is connected with the guide member through the water inlet hole, and is connected with the water storage cavity through the water outlet hole;
the electrode is arranged in the water collecting cavity.

30. The air purifier of claim 1, wherein the purifying member comprises a photocatalyst layer; the photocatalyst layer is arranged on at least one of a surface of the purifying member and an inner wall surface of the accommodating cavity, and configured to be exposed to light.

31. The air purifier of claim 30, wherein the purifying member comprises: a sterilization lamp arranged in the accommodating cavity to illuminate the photocatalyst layer.

32. The air purifier of claim 1, wherein the purifying member comprises a fan arranged above the purifying assembly to drive the air to flow from the air inlet to the air outlet via the purifying assembly; the driving device is connected with the fan to drive the fan into rotation.

33. The air purifier of claim 1, wherein the air moving member comprises:
a support frame, which is arranged on an inner wall of the accommodating cavity, an upper end of the purifying member being fixed on a lower side of the support frame;
a blower, which is fixed on the support frame; and
a filtering member, which is arranged above the blower.

34. The air purifier of claim 33, wherein the blower is a multi-vane centrifugal blower.

35. The air purifier of claim 33, wherein the air moving member comprises a second grille arranged at the air outlet.

36. The air purifier of claim 33, further comprising: a watertight structure, which is fixedly connected with an inner wall of the accommodating cavity and is in communication with the water storage cavity; an accommodating space is defined in the watertight structure, and a volume of the accommodating space is greater than a volume of the water storage cavity.

37. The air purifier of claim 36, wherein the watertight structure comprises:
   an accommodating member, a flow collecting part being arranged on the accommodating member, the flow collecting part defining a flow collecting groove which is provided with a drainage mouth; and
   a directing member, a drainage channel being defined in the directing member, one end of the drainage channel being in communication with the drainage mouth and another end being in communication with the water storage cavity.

38. The air purifier of claim 37, wherein the accommodating member comprises:
   a cylindrical body, which is connected with the inner wall of the accommodating cavity;
   an upper retainer ring, which is arranged on a upper end of the cylindrical body and shields a gap between an outer circumference of the blower and the inner wall of the accommodating cavity, a support frame being arranged on the upper retainer ring; and
   a lower retainer ring, which is arranged on a lower end of the cylindrical body, and forms the flow collecting part; an annular accommodating space is defined between the inner wall of the cylindrical body, the flow collecting part and the upper retainer ring.

39. The air purifier of claim 1, wherein the housing comprises a first housing, a second housing and a third housing which are detachably connected to one another; the first housing is located above the third housing; the second housing is connected between the first housing and the second housing; the air moving member is located in the first housing; the purifying member is located in the second housing; and the water supply member is located in the third housing.

40. The air purifier of claim 39, wherein the air inlet is arranged on a side wall of the third housing, and an edge of the air inlet forms a chamfer extending along an air inflow direction.

41. An air purifier, comprising:
   a housing provided with an air inlet and an air outlet and defining an accommodating cavity communicating the air inlet with the air outlet, the air inlet being located on a side wall of the housing;
   a water supply member arranged in the accommodating cavity, a water storage cavity being defined in the water supply member;
   a purifying member, the purifying member being arranged in the accommodating cavity and located above the water supply member to purify air, the purifying member comprising:
      a purifying assembly rotatably arranged in the accommodating cavity,
      a water distribution assembly for guiding water in the water supply member to flow upwards and distributing water towards the purifying assembly, and
      a driving device located above the purifying assembly and connected with the purifying assembly to drive the purifying assembly into rotation; and
   an air moving member arranged in the accommodating cavity and located above the purifying member, wherein a wire access pipe extending in an axial direction is arranged in the accommodating cavity.

* * * * *